(12) United States Patent
Kimoto et al.

(10) Patent No.: US 10,836,745 B2
(45) Date of Patent: Nov. 17, 2020

(54) COCRYSTAL, PRODUCTION METHOD THEREOF, AND MEDICAMENT CONTAINING COCRYSTAL

(71) Applicant: Takeda Pharmaceutical Company Limited, Chuo-ku, Osaka-shi, Osaka (JP)

(72) Inventors: Koya Kimoto, Kanagawa (JP); Mitsuo Yamamoto, Kanagawa (JP); Masato Kitayama, Osaka (JP); Yasuhiro Sawai, Osaka (JP); Miyuki Hohokabe, Osaka (JP); Kentaro Iwata, Kanagawa (JP)

(73) Assignee: Takeda Pharmaceutical Company Limited, Osaka (JP)

( * ) Notice: Subject to any disclaimer, the term of this patent is extended or adjusted under 35 U.S.C. 154(b) by 25 days.

(21) Appl. No.: 15/388,063

(22) Filed: Dec. 22, 2016

(65) Prior Publication Data

US 2017/0183326 A1 Jun. 29, 2017

(30) Foreign Application Priority Data

Dec. 24, 2015 (JP) ................ 2015-252658

(51) Int. Cl.
| | |
|---|---|
| C07D 401/14 | (2006.01) |
| C07C 59/54 | (2006.01) |
| A61K 31/4725 | (2006.01) |
| C07C 55/08 | (2006.01) |
| C07C 57/145 | (2006.01) |
| C07C 59/245 | (2006.01) |
| C07C 59/265 | (2006.01) |
| C07C 59/50 | (2006.01) |
| C07C 65/05 | (2006.01) |
| C07C 65/10 | (2006.01) |

(52) U.S. Cl.
CPC ........ *C07D 401/14* (2013.01); *A61K 31/4725* (2013.01); *C07C 55/08* (2013.01); *C07C 57/145* (2013.01); *C07C 59/245* (2013.01); *C07C 59/265* (2013.01); *C07C 59/50* (2013.01); *C07C 59/54* (2013.01); *C07C 65/05* (2013.01); *C07C 65/10* (2013.01); *C07B 2200/13* (2013.01)

(58) Field of Classification Search
CPC .................................... C07D 401/14
USPC .......................... 546/143; 514/310
See application file for complete search history.

(56) References Cited

U.S. PATENT DOCUMENTS

| | | |
|---|---|---|
| 6,894,051 B1 | 5/2005 | Zimmermann et al. |
| 7,718,662 B1 | 5/2010 | Chen et al. |
| 9,138,436 B2 | 9/2015 | Chen et al. |
| 2002/0115858 A1 | 8/2002 | Zimmermann et al. |
| 2003/0087927 A1 | 5/2003 | Sieger et al. |
| 2003/0130331 A1 | 7/2003 | Donsbach et al. |
| 2004/0162327 A1 | 8/2004 | Donsbach et al. |
| 2005/0192284 A1 | 9/2005 | Zimmermann et al. |
| 2006/0030568 A1 | 2/2006 | Zimmermann et al. |
| 2006/0276526 A1 | 12/2006 | Donsbach et al. |
| 2007/0004746 A1 | 1/2007 | Zimmermann et al. |
| 2007/0026078 A1 | 2/2007 | Almarsson et al. |
| 2009/0031844 A1 | 2/2009 | Iwakawa et al. |
| 2014/0256734 A1 | 9/2014 | Lawson et al. |
| 2016/0310483 A1 | 10/2016 | Lawson et al. |

FOREIGN PATENT DOCUMENTS

| | | |
|---|---|---|
| WO | WO 99/18097 A1 | 4/1999 |
| WO | WO 2011/067571 A1 | 6/2011 |
| WO | WO 2014/164558 A1 | 10/2014 |

OTHER PUBLICATIONS

Halebian et al., Pharmaceutical Applications, etc., Pharmaceutical Sciences 58(8), 1969, 911-929.*
Dean "Analytical Chem . . . " p. 10.24-10.26 (1995).*
Seddon "Pseudopolymorph . . . " Crystal Growth & design v.4(6) p. 1087 (2004) (2 pages from internet).*
Ivanisevic et al., "Use of X-ray . . . "Pharm. Sci. Encycl. p. 1-42 (2010).*
Ivanisevic et al., "Uses of X-ray, etc.," Pharm. Form. Qual. 2011, pp. 30-33.*
Bhattacharya et al., "Thermoanalytical and Crystallographic Methods" in Brittain H. ed., 2nd ed. Informa Healthcare:NY 2009 p. 318-335.*
Aakeroy, "Crystal Engineering, etc.," Acta Cryst. (1997) B53, 569-586.*
Sekhon BS, "Pharmaceutical co-cyrstals, etc." Ars Pharm., 50(2): 99-117 (2009).*
Kirk-Othmer Encyclopedia of Chemical Technology, 8, pp. 95-147 (2002).*
Stahly, "Diversity in Single-, etc.", Crystal Growth & Design, 7 (6), 2007, 1007-1026.*
Vippagunta et al., "Crystalline Solids", Advanced Drug Delivery Reviews 48 (2001) 3-26.*
Braga et al., "Making crystals from . . . " J. Royal Soc. Chem. Commun. p. 3635-3645 (2005).*
Davidovich et al., "Detection of polymorphism . . . " Am. Pharm. Rev. v.&(1) p. 10, 12, 14, 16, 100 (2004).*
Weyna et al., "Synthesis and Structural, etc.," Crystal Growth & Design, 2009, 9(2), 1106-1123.*
Stilinovic et al., "Salts and Co-Crystals, etc.," Crystal Growth & Design, 2012, 12, 5763-5772.*
Yadav et al., "Co-crystals: A novel approach to modify physicochemical properties of active pharmaceutical ingredients," Indian Journal of Pharmaceutical Sciences, 2009, 71(4):359-370.

(Continued)

*Primary Examiner* — Patricia L Morris
(74) *Attorney, Agent, or Firm* — Foley & Lardner LLP

(57) ABSTRACT

The present invention provides a cocrystal of (S)-3-(1-((1-acryloylpyrrolidin-3-yl)oxy)isoquinolin-3-yl)-1H-1,2,4-triazol-5(4H)-one and an organic acid capable of forming a cocrystal with the compound.

10 Claims, 7 Drawing Sheets

(56) References Cited

OTHER PUBLICATIONS

Yamamoto et al., "Establishment of cocrystal cocktail grinding method for rational screening of pharmaceutical cocrystals," International Journal of Pharmaceutics, 2012, 437:162-171.
Shan et al., "The role of cocrystals in pharmaceutical science," Drug Discovery Today, May 2008, 13(9/10):440-446.
Trask, A.V., "An overview of Pharmaceutical Cocrystals as Intellectual Property," Molecular Pharmaceutics, 2007, 4(3):301-309.
Kojima et al., "Application of in situ Raman Microscopy to Cocrystal Screening,"Journal of Pharmaceutical Machinery and Engineering, 2012, 21:23-28, with English abstract.
Schultheiss et al,. "Pharmaceutical Cocrystals and Their Physicochemical Properties," Crystal Growth & Design, 2009, 9(6):2950-2967.
Takata, Noriyuki, "Cocrystal screening and its application in the improvement of the physical properties of active pharmaceutical ingredients," Pharm. Tech. Japan, 2009, 25(12):155-166, with English abstract.
Vishweshwar et al., "Pharmaceutical Co-Crystals," Journal of Pharmaceutical Sciences, 2006, 95(3):499-516.

\* cited by examiner

COCRYSTAL, PRODUCTION METHOD THEREOF, AND MEDICAMENT CONTAINING COCRYSTAL

TECHNICAL FIELD

The present invention relates to a cocrystal of (S)-3-(1-((1-acryloylpyrrolidin-3-yl)oxy)isoquinolin-3-yl)-1H-1,2,4-triazol-5(4H)-one and a production method thereof.

BACKGROUND OF THE INVENTION

Patent document 1 describes a compound represented by the formula 1:

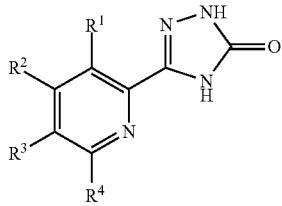

wherein each group is as defined in patent document 1 (hereinafter sometimes to be abbreviated as "compound 1") as a pyridinyl triazolone derivative or a fused pyridinyl triazolone derivative, which is an inhibitor of Bruton's tyrosine kinase (hereinafter sometimes to be abbreviated as "BTK"). Also, in Example 5 of patent document 1, (S)-3-(1-((1-acryloylpyrrolidin-3-yl)oxy)isoquinolin-3-yl)-1H-1,2,4-triazol-5(4H)-one represented by the following formula:

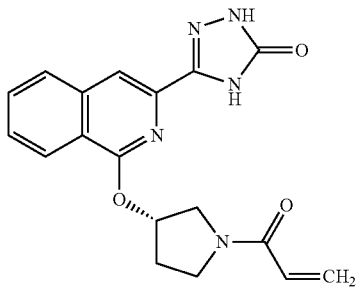 [SMILES: C=CC(=O)N1CC[C@H](Oc2nc(-c3n[nH]c(=O)[nH]3)cc3ccccc23)C1]

(hereinafter sometimes to be abbreviated as "compound (A)") is produced as one embodiment of compound 1.

In addition, paragraph [0083] of patent document 1 describes that compound 1 may be present as a cocrystal. Cocrystal generally means a crystal in which multicomponents constituting the cocrystal are bonded by a bond or interaction other than an ionic bond (e.g., a hydrogen bond, Van der Waals' force, a π-π bond, etc.), and is distinguished from a salt in which multicomponents are bonded by an ionic bond.

DOCUMENT LIST

Patent Document patent document 1: WO 2014/164558

SUMMARY OF THE INVENTION

Problems to be Solved by the Invention

An object of the present invention is to improve dissolution property and oral absorbability of compound (A).

Means of Solving the Problems

The present inventors have conducted intensive studies and found that a cocrystal of compound (A) and an organic acid capable of forming a cocrystal with compound (A) shows improved dissolution property as compared to compound (A). The present invention based on this finding is as described below.

[1] A cocrystal of (S)-3-(1-((1-acryloylpyrrolidin-3-yl)oxy)isoquinolin-3-yl)-1H-1,2,4-triazol-5(4H)-one and an organic acid capable of forming a cocrystal with the aforementioned compound.

[2] The cocrystal of the aforementioned [1], wherein the organic acid is a carboxylic acid.

[3] The cocrystal of the aforementioned [2], wherein the carboxylic acid is a compound represented by the formula (I):

{wherein
X is a hydroxy group or a carboxy group, and
$R^1$ is a divalent group represented by the formula (Ia):

{wherein,
$R^2$ and $R^3$ are each independently a hydrogen atom or an optionally substituted $C_{1-6}$ alkyl group, or bonded to each other to form, together with the carbon atoms bonded thereto, an optionally substituted $C_{6-14}$ hydrocarbon ring,
* is a binding position to HOOC, and
** is a binding position to X}, or a divalent group represented by the formula (Ib):

{wherein,
$R^4$ and $R^5$ are each independently a hydrogen atom, an optionally substituted $C_{1-6}$ alkyl group, or an optionally substituted $C_{6-14}$ aryl group,
* is a binding position to HOOC, and
** is a binding position to X}.

[4] The cocrystal of the aforementioned [3], wherein the optionally substituted $C_{1-6}$ alkyl group is a $C_{1-6}$ alkyl group optionally having at least one substituent selected from the group consisting of a hydroxy group and a carboxy group.

[5] The cocrystal of the aforementioned [3], wherein the optionally substituted $C_{6-14}$ hydrocarbon ring is a benzene ring optionally having at least one substituent selected from the group consisting of a hydroxy group and a carboxy group.

[6] The cocrystal of the aforementioned [3], wherein the optionally substituted $C_{6-14}$ aryl group is a phenyl optionally having at least one substituent selected from the group consisting of a hydroxy group and a carboxy group.

[7] The cocrystal of the aforementioned [3], wherein the compound represented by the formula (I) is gentisic acid, salicylic acid, maleic acid, malonic acid, malic acid, mandelic acid or citric acid.

[8] The cocrystal of the aforementioned [3], wherein the compound represented by the formula (I) is gentisic acid, salicylic acid or maleic acid.

[9] The cocrystal of the aforementioned [3], wherein the compound represented by the formula (I) is gentisic acid.

[10] The cocrystal of the aforementioned [9], wherein a molar ratio of (S)-3-(1-((1-acryloylpyrrolidin-3-yl)oxy)isoquinolin-3-yl)-1H-1,2,4-triazol-5(4H)-one and gentisic acid ((S)-3-(1-((1-acryloylpyrrolidin-3-yl)oxy)isoquinolin-3-yl)-1H-1,2,4-triazol-5(4H)-one:gentisic acid) is 1:0.5-1:5.

[11] A medicament comprising the cocrystal of any one of the aforementioned [1]-[10].

[12] A method of producing the cocrystal of the aforementioned [3], comprising mixing and stirring a strongly basic aqueous solution of (S)-3-(1-((1-acryloylpyrrolidin-3-yl)oxy)isoquinolin-3-yl)-1H-1,2,4-triazol-5(4H)-one, and a solution of a compound represented by the formula (I):

$$HOOC-R^1-X \qquad (I)$$

wherein
X is a hydroxy group or a carboxy group, and
$R^1$ is a divalent group represented by the formula (Ia):

{wherein,
$R^2$ and $R^3$ are each independently a hydrogen atom or an optionally substituted $C_{1-6}$ alkyl group, or bonded to each other to form, together with the carbon atoms bonded thereto, an optionally substituted $C_{6-14}$ hydrocarbon ring,
* is a binding position to HOOC, and
** is a binding position to X}, or a divalent group represented by the formula (Ib):

{wherein,
$R^4$ and $R^5$ are each independently a hydrogen atom, an optionally substituted $C_{1-6}$ alkyl group, or an optionally substituted $C_{6-14}$ aryl group,
* is a binding position to HOOC, and
** is a binding position to X}.

[13] The production method of the aforementioned [12], wherein the compound represented by the formula (I) in the mixed solution of the strongly basic aqueous solution of (S)-3-(1-((1-acryloylpyrrolidin-3-yl)oxy)isoquinolin-3-yl)-1H-1,2,4-triazol-5(4H)-one and the solution of the compound represented by the formula (I) has a concentration of 0.298-0.592 mol/L.

[14] The production method of the aforementioned [12], wherein the compound represented by the formula (I) in the mixed solution of the strongly basic aqueous solution of (S)-3-(1-((1-acryloylpyrrolidin-3-yl)oxy)isoquinolin-3-yl)-1H-1,2,4-triazol-5(4H)-one and the solution of the compound represented by the formula (I) has a concentration of 0.388-0.592 mol/L.

[15] The production method of the aforementioned [12], wherein a solvent of the solution of the compound represented by the formula (I) is
(i) water,
(ii) at least one organic solvent selected from the group consisting of isopropyl alcohol, dimethyl sulfoxide, N,N-dimethylformamide, N,N-dimethylacetamide, methanol, ethanol, 1-propanol, tetrahydrofuran, acetone, 2,2,2-trifluoroethanol, acetonitrile, 1-methyl-2-pyrrolidone, and acetic acid, or (iii) a mixed solvent of at least one organic solvent selected from the group described in (ii) and water.

[16] The production method of the aforementioned [12], comprising adding, as a seed crystal, a cocrystal of (S)-3-(1-((1-acryloylpyrrolidin-3-yl)oxy)isoquinolin-3-yl)-1H-1,2,4-triazol-5(4H)-one and a compound represented by the formula (I) to the mixture of the strongly basic aqueous solution of (S)-3-(1-((1-acryloylpyrrolidin-3-yl)oxy)isoquinolin-3-yl)-1H-1,2,4-triazol-5(4H)-one and the solution of the compound represented by the formula (I).

[17] The production method of any one of the aforementioned [12]-[16], wherein the compound represented by the formula (I) is gentisic acid, salicylic acid, maleic acid, malonic acid, malic acid, mandelic acid or citric acid.

[18] The production method of any one of the aforementioned [12]-[16], wherein the compound represented by the formula (I) is gentisic acid, salicylic acid or maleic acid.

[19] The production method of any one of the aforementioned [12]-[16], wherein the compound represented by the formula (I) is gentisic acid.

Effect of the Invention

The dissolution property and oral absorbability of compound (A) can be improved by converting compound (A) to a cocrystal of compound (A) and an organic acid capable of forming a cocrystal with compound (A).

DETAILED DESCRIPTION OF THE INVENTION

Figure 1:
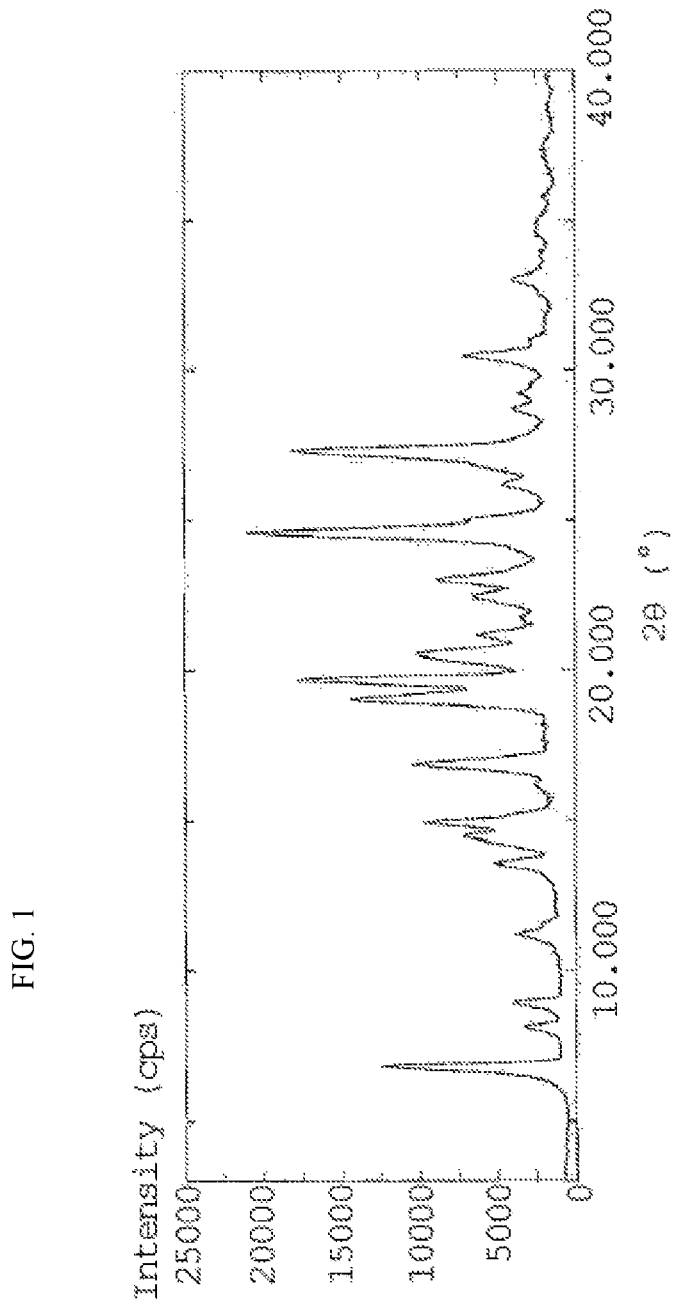
FIG. 1 is a powder X-ray diffraction chart of the cocrystals of compound (A) and gentisic acid, which were obtained in Production Example 2.

The present invention provides a cocrystal of compound (A) and an organic acid capable of forming a cocrystal with compound (A). The cocrystal of the present invention is superior in the dissolution property (solubility and dissolution rate) as compared to compound (A), as shown in the following Experimental Examples. The cocrystal of the present invention superior in the dissolution property is also superior in the oral absorbability. The cocrystal of the present invention may be a nonhydrate or a hydrate.

As the organic acid capable of forming a cocrystal with compound (A), a carboxylic acid is preferable, and a compound represented by the formula (I):

HOOC—R$^1$—X    (I)

wherein
X is a hydroxy group or a carboxy group, and
R$^1$ is a divalent group represented by the formula (Ia):

*—C(R$^2$)=C(R$^3$)—**    (Ia)

{wherein,
R$^2$ and R$^3$ are each independently a hydrogen atom or an optionally substituted C$_{1-6}$ alkyl group, or bonded to each other to form, together with the carbon atoms bonded thereto, an optionally substituted C$_{6-14}$ hydrocarbon ring,
* is a binding position to HOOC, and
** is a binding position to X}, or a divalent group represented by the formula (Ib):

*—C(R$^4$)(R$^5$)—**    (Ib)

{wherein,
R$^4$ and R$^5$ are each independently a hydrogen atom, an optionally substituted C$_{1-6}$ alkyl group, or an optionally substituted C$_{6-14}$ aryl group,
* is a binding position to HOOC, and
** is a binding position to X}
(hereinafter sometimes to be abbreviated as "compound (I)") is more preferable.

Compound (I) has a combination of a carboxy group (HOOC—) and a hydroxy group or carboxy group (—X), as shown in the formula (I). These two groups form a hydrogen bond with a nitrogen atom and a carbonyl group of compound (A), which is considered to contribute to the formation of a cocrystal of compound (A) and compound (I).

In the present specification, examples of the "C$_{1-6}$ alkyl group" include methyl, ethyl, propyl, isopropyl, butyl, isobutyl, sec-butyl, tert-butyl, pentyl, isopentyl, neopentyl, 1-ethylpropyl, hexyl, isohexyl, 1,1-dimethylbutyl, 2,2-dimethylbutyl, 3,3-dimethylbutyl and 2-ethylbutyl.

In the present specification, examples of the "C$_{6-14}$ aryl group" include phenyl, 1-naphthyl, 2-naphthyl, 1-anthryl, 2-anthryl and 9-anthryl.

In the present specification, examples of the "C$_{6-14}$ hydrocarbon ring" include a C$_{5-14}$ aromatic hydrocarbon ring, a C$_{3-10}$ cycloalkane and a C$_{3-10}$ cycloalkene.

In the present specification, examples of the "C$_{6-14}$ aromatic hydrocarbon ring" include benzene and naphthalene.

In the present specification, examples of the "C$_{3-10}$ cycloalkane" include cyclopropane, cyclobutane, cyclopentane, cyclohexane, cycloheptane and cyclooctane.

In the present specification, examples of the "C$_{3-10}$ cycloalkene" include cyclopropene, cyclobutene, cyclopentene, cyclohexene, cycloheptene and cyclooctene.

The substituent that the optionally substituted C$_{1-6}$ alkyl group, the optionally substituted C$_{6-14}$ aryl group and the optionally substituted C$_{6-14}$ hydrocarbon ring in the formula (I) may have is preferably a nonbasic group. When compound (I) has a basic group, the basic group and a proton dissociated from a carboxy group of compound (I) are bonded to form a salt, which may inhibit formation of a cocrystal of compound (I) and compound (A).

Examples of the substituent that the optionally substituted C$_{1-6}$ alkyl group may have include a halogen atom (e.g., fluorine, chlorine, bromine, iodine), a nitro group, a cyano group, an oxo group, a hydroxy group, a formyl group, a carboxy group and a sulfo group. The optionally substituted C$_{1-6}$ alkyl group is preferably a C$_{1-6}$ alkyl group optionally having at least one substituent selected from the group consisting of a hydroxy group and a carboxy group.

Examples of the substituent that the optionally substituted C$_{6-14}$ aryl group may have include a halogen atom (e.g., fluorine, chlorine, bromine, iodine), a nitro group, a cyano group, an oxo group, a hydroxy group, a formyl group, a carboxy group, a sulfo group and an optionally substituted C$_{1-6}$ alkyl group. The optionally substituted C$_{6-14}$ aryl group is preferably phenyl optionally having at least one substituent selected from the group consisting of a hydroxy group and a carboxy group.

Examples of the substituent that the optionally substituted C$_{6-14}$ hydrocarbon ring may have include a halogen atom (e.g., fluorine, chlorine, bromine, iodine), a nitro group, a cyano group, an oxo group, a hydroxy group, a formyl group, a carboxy group, a sulfo group and an optionally substituted C$_{1-6}$ alkyl group. The optionally substituted C$_{6-14}$ hydrocarbon ring is preferably a benzene ring optionally having at least one substituent selected from the group consisting of a hydroxy group and a carboxy group.

Compound (I) is preferably gentisic acid, salicylic acid, maleic acid, malonic acid, malic acid, mandelic acid or citric acid, each represented by the following formula. The malic acid may be L-malic acid, D-malic acid or a mixture thereof, preferably L-malic acid. The mandelic acid may be L-mandelic acid, D-mandelic acid or a mixture thereof, preferably DL-mandelic acid (i.e., (+/−)-mandelic acid).

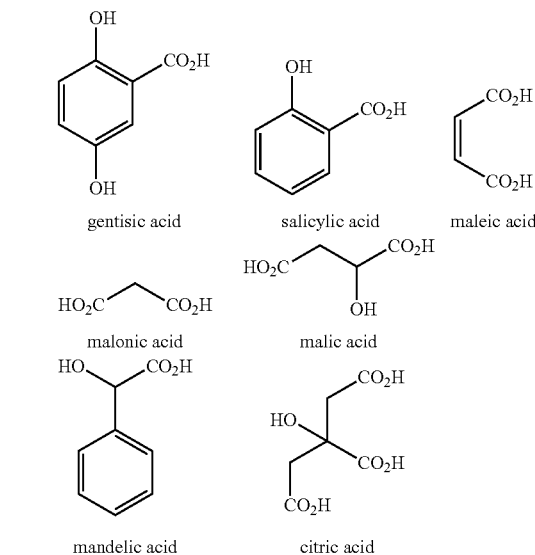

Compound (I) is more preferably gentisic acid, salicylic acid or maleic acid, further preferably gentisic acid. The cocrystal of compound (A) and gentisic acid may be a nonhydrate or a hydrate. The cocrystal of compound (A) and gentisic acid is preferably a nonhydrate, a monohydrate or a trihydrate, more preferably a nonhydrate.

The molar ratio of compound (A) and gentisic acid (compound (A):gentisic acid) in the cocrystal of these is preferably 1:0.5-1:5, more preferably 1:0.9-1:3.1, further preferably 1:1 or 1:3, particularly preferably 1:1.

When powder X-ray diffraction is measured under the conditions described in the below-mentioned Examples, a cocrystal of compound (A) and gentisic acid is preferably a cocrystal showing a powder X-ray diffraction pattern having characteristic peaks at lattice spacings (d) of about 13.04±0.2, 5.96±0.2, 4.67±0.2, 3.63±0.2 and 3.28±0.2 angstroms, more preferably a cocrystal showing a powder X-ray diffraction pattern having characteristic peaks at lattice spacings (d) of about 13.04±0.2, 10.92±0.2, 9.97±0.2, 5.96±0.2, 4.67±0.2, 3.63±0.2 and 3.28±0.2 angstroms, further preferably a cocrystal showing a powder X-ray diffraction pattern having characteristic peaks at lattice spacings (d) of about 13.04±0.2, 10.92±0.2, 9.97±0.2, 6.14±0.2, 5.96±0.2, 5.28±0.2, 4.67±0.2, 3.63±0.2 and 3.28±0.2 angstroms. The molar ratio of compound (A) and gentisic acid (compound (A):gentisic acid) in a cocrystal showing such powder X-ray diffraction pattern is 1:1. A cocrystal showing such powder X-ray diffraction pattern is a nonhydrate.

When powder X-ray diffraction is measured under the conditions described in the below-mentioned Examples, another cocrystal of compound (A) and gentisic acid is preferably a cocrystal showing a powder X-ray diffraction pattern having characteristic peaks at lattice spacings (d) of about 25.97±0.2, 13.06±0.2, 6.54±0.2, 5.24±0.2 and 5.02±0.2 angstroms, more preferably a cocrystal showing a powder X-ray diffraction pattern having characteristic peaks at lattice spacings (d) of about 25.97±0.2, 13.06±0.2, 7.64±0.2, 7.08±0.2, 6.54±0.2, 5.24±0.2 and 5.02±0.2 angstroms, further preferably a cocrystal showing a powder X-ray diffraction pattern having characteristic peaks at lattice spacings (d) of about 25.97±0.2, 13.06±0.2, 7.98±0.2, 7.64±0.2, 7.08±0.2, 6.54±0.2, 6.01±0.2, 5.24±0.2 and 5.02±0.2 angstroms. The molar ratio of compound (A) and gentisic acid (compound (A):gentisic acid) in a cocrystal showing such powder X-ray diffraction pattern is 1:3. A cocrystal showing such powder X-ray diffraction pattern is a trihydrate.

When powder X-ray diffraction is measured under the conditions described in the below-mentioned Examples, a still another cocrystal of compound (A) and gentisic acid is preferably a cocrystal showing a powder X-ray diffraction pattern having characteristic peaks at lattice spacings (d) of about 25.08±0.2, 6.83±0.2, 6.25±0.2, 5.25±0.2 and 5.01±0.2 angstroms, more preferably a cocrystal showing a powder X-ray diffraction pattern having characteristic peaks at lattice spacings (d) of about 25.08±0.2, 7.20±0.2, 6.83±0.2, 6.42±0.2, 6.25±0.2, 5.25±0.2 and 5.01±0.2 angstroms, further preferably a cocrystal showing a powder X-ray diffraction pattern having characteristic peaks at lattice spacings (d) of about 25.08±0.2, 9.02±0.2, 7.20±0.2, 6.83±0.2, 6.42±0.2, 6.25±0.2, 5.98±0.2, 5.25±0.2 and 5.01±0.2 angstroms. The molar ratio of compound (A) and gentisic acid (compound (A):gentisic acid) in a cocrystal showing such powder X-ray diffraction pattern is 1:3. A cocrystal showing such powder X-ray diffraction pattern is a monohydrate.

The present invention also provides a production method of a cocrystal of compound (A). The cocrystal can be produced by adding compound (A) to a saturated solution of an organic acid capable of forming a cocrystal with compound (A) (preferably a carboxylic acid, more preferably compound (I)) and stirring the mixture. The production method of this embodiment (hereinafter sometimes to be abbreviated as "production method 1") is explained below by using compound (I) as a representative example of an organic acid capable of forming a cocrystal with compound (A).

Examples of the solvent of the saturated solution of compound (I) include acetonitrile, dimethyl sulfoxide (DMSO), dimethylacetamide (DMAc), methanol, ethanol, isopropanol, tetrahydrofuran (THF), acetone, ethyl acetate, N-methylpyrrolidone (NMP), acetic acid and water. Only one kind of solvent may be used or two or more kinds thereof may be used in combination. Of these, acetonitrile is preferable.

In production method 1, the amount of the saturated solution of compound (I) to be used is preferably 1-1000 mL, more preferably 10-100 mL, relative to 1 g of compound (A). While the stirring rate varies depending on the scale of the instrument to be used, it is, for example, 1-1200 rpm, preferably 20-600 rpm. The stirring temperature is preferably 0-100° C., more preferably 20-30° C. The stirring time is preferably 2 hr-6 days, more preferably 1 day-6 days.

The cocrystal of compound (A) can also be produced by mixing a strongly basic aqueous solution of compound (A) and a solution of an organic acid capable of forming a cocrystal with compound (A) (preferably carboxylic acid, more preferably compound (I)), and stirring the mixture. The production method of this embodiment (hereinafter sometimes to be abbreviated as "production method 2") is explained below by using compound (I) as a representative example of an organic acid capable of forming a cocrystal with compound (A).

Only one kind of strong base may be used or two or more kinds thereof may be used in combination. Examples of the strong base include sodium hydroxide, potassium hydroxide, lithium hydroxide and cesium hydroxide. Of these, sodium hydroxide or potassium hydroxide is preferable, sodium hydroxide is more preferable.

The concentration of compound (A) in the strongly basic aqueous solution is preferably 0.010-0.200 mol/L, more preferably 0.100-0.200 mol/L, further preferably 0.150-0.200 mol/L. The concentration of the strong base in the strongly basic aqueous solution is preferably 0.010-0.200 mol/L, more preferably 0.100-0.200 mol/L, further preferably 0.150-0.200 mol/L.

In production method 2, examples of the solvent of the solution of compound (I) include the following:
(i) water,
(ii) at least one organic solvent selected from the group consisting of isopropyl alcohol, dimethyl sulfoxide, N,N-dimethylformamide, N,N-dimethylacetamide, methanol, ethanol, 1-propanol, tetrahydrofuran, acetone, 2,2,2-trifluoroethanol, acetonitrile, 1-methyl-2-pyrrolidone and acetic acid, or
(iii) a mixed solvent of at least one organic solvent selected from the group described in (ii) and water.

As a solvent of a solution of compound (I), a mixed solvent of the organic solvent of the above-mentioned (iii) and water is preferable, a mixed solvent of isopropyl alcohol and water is more preferable. The amount of the organic solvent (particularly, isopropyl alcohol) in the mixed solvent is preferably 1-99% by volume, more preferably 30-70% by volume, further preferably 45-55% by volume.

In production method 2, the concentration of compound (I) in a mixed solution of a strongly basic aqueous solution of compound (A) and a solution of compound (I) is preferably 0.298-0.592 mol/L, more preferably 0.388-0.592 mol/L, further preferably 0.388-0.479 mol/L.

In production method 2, the amount of compound (I) to be used is preferably 2.3-5.2 mol, more preferably 3.0-5.2 mol, further preferably 3.0-4.0 mol, relative to 1 mol of compound (A). While the stirring rate of the mixed solution varies depending on the scale of the instrument to be used, it is, for example, 1-1200 rpm, preferably 20-600 rpm. The stirring temperature is preferably 0-100° C., more preferably 20-30° C. The stirring time is preferably 0.1 hr-10 days, more preferably 0.5 day-3 days.

In production method 2, while a mixing method of the strongly basic aqueous solution of compound (A) and the solution of compound (I) is not particularly limited, the solution of compound (I) is preferably added dropwise to a strongly basic aqueous solution of compound (A) and the mixture is mixed.

In production method 2, the mixture of the strongly basic aqueous solution of compound (A) and the solution of compound (I) may be irradiated with ultrasonic waves before, during or after stirring the mixture. The ultrasonic irradiation time is preferably 1 min-3 days, more preferably 1-3 hr.

In production method 2, to promote precipitation of the cocrystal, a cocrystal of compound (A) and compound (I) is preferably added as a seed crystal to the mixture of the strongly basic aqueous solution of compound (A) and the solution of compound (I). The amount of the seed crystal (cocrystal) to be added is preferably 0.1-200 mg, more preferably 0.5-50 mg, further preferably 0.5-10 mg, relative to 1 g of compound (A). As the seed crystal, the cocrystal prepared in advance in production method 1 or 2 can be used. While the timing of addition of the seed crystal is not particularly limited, it is preferably added after mixing the strongly basic aqueous solution of compound (A) and the solution of compound (I) and before stirring of the mixture.

The present invention also provides a medicament (pharmaceutical composition or formulation) containing the cocrystal of the present invention. In the following explanation, the following definitions are used unless specifically described.

"Subject" refers to a mammal, including a human.

"Pharmaceutically acceptable" substances refer to those substances which are suitable for administration to subjects.

"Treating" refers to reversing, alleviating, inhibiting the progress of, or preventing a disease, disorder or condition to which such term applies, or to reversing, alleviating, inhibiting the progress of, or preventing one or more symptoms of such disorder, disease or condition.

"Treatment" refers to the act of the "treating", as defined immediately above.

"Drug", "drug substance", "active pharmaceutical ingredient", and the like, refer to a compound that may be used for treating a subject in need of treatment.

"Effective amount" of a drug, "therapeutically effective amount" of a drug, and the like, refer to the quantity of the drug that may be used for treating a subject and may depend on the weight and age of the subject and the route of administration, among other things.

"Excipient" refers to any diluent or vehicle for a drug.

"Pharmaceutical composition" refers to the combination of one or more drug substances and one or more excipients.

"Drug product", "pharmaceutical dosage form", "dosage form", "final dosage form" and the like, refer to a pharmaceutical composition suitable for treating a subject in need of treatment and generally may be in the form of tablets, capsules, sachets containing powder or granules, liquid solutions or suspensions, patches, films, and the like.

"Condition associated with BTK" and similar phrases relate to a disease, disorder or condition in a subject for which inhibition of BTK may provide a therapeutic or prophylactic benefit.

The cocrystals of the present invention may be administered alone, or in combination with each other, or with one or more pharmacologically active compounds which are different from the cocrystals of the present invention. Generally, the cocrystals of the present invention and one or more of these compounds are administered as a pharmaceutical composition (formulation) in association with one or more pharmaceutically acceptable excipients. The choice of excipients depends on a particular mode of administration, the effect of the excipient on solubility and stability, and the nature of the dosage form, among other things. Useful pharmaceutical compositions and methods for their preparation may be found, for example, in A. R. Gennaro (ed.), *Remington: The Science and Practice of Pharmacy* (20th ed., 2000).

The cocrystals of the present invention may be administered orally. Oral administration may involve swallowing in which case compound (A) enters the bloodstream via the gastrointestinal tract. Alternatively or additionally, oral administration may involve mucosal administration (e.g., buccal, sublingual, supralingual administration) such that compound (A) enters the bloodstream through the oral mucosa.

Formulations suitable for oral administration include solid, semi-solid and liquid systems such as tablets; soft or hard capsules containing multi-particulates or nano-particulates, liquids, or powders; lozenges which may be liquid-filled; chews; gels; fast dispersing dosage forms; films; ovules; sprays; and buccal or mucoadhesive patches. Liquid formulations include suspensions, solutions, syrups and elixirs. Such formulations may be employed as fillers in soft or hard capsules (made, e.g., from gelatin or hydroxypropylmethylcellulose) and typically comprise a carrier (e.g., water, ethanol, polyethylene glycol, propylene glycol, methylcellulose, a suitable oil) and one or more emulsifying agents, suspending agents or both. Liquid formulations may also be prepared by the reconstitution of a solid (e.g., from a sachet).

The cocrystals of the present invention may also be used in fast-dissolving and fast-disintegrating dosage forms such as those described in Liang and Chen, *Expert Opinion in Therapeutic Patents* (2001) 11(6):981-986.

For tablet dosage forms, depending on dose, the active pharmaceutical ingredient (hereinafter sometimes to be abbreviated as "API") may comprise from about 1 wt % to about 80 wt % of the dosage form, more typically from about 5 wt % to about 60 wt % of the dosage form. In addition to the API, tablets may include one or more disintegrants, binders, diluents, surfactants, glidants, lubricants, anti-oxidants, colorants, flavoring agents, preservatives and taste-masking agents. Examples of disintegrants include sodium starch glycolate, sodium carboxymethyl cellulose, calcium carboxymethyl cellulose, croscarmellose sodium, crospovidone, polyvinylpyrrolidone, methyl cellulose, microcrystalline cellulose, $C_{1-6}$ alkyl-substituted hydroxypropylcellulose, starch, pregelatinized starch and sodium alginate. Generally, the disintegrant will comprise from about 1 wt % to about 25 wt %, preferably from about 5 wt % to about 20 wt % of the dosage form.

Binders are generally used to impart cohesive qualities to a tablet formulation. Suitable binders include microcrystalline cellulose, gelatin, sugars, polyethylene glycol, natural and synthetic gums, polyvinylpyrrolidone, pregelatinized starch, hydroxypropylcellulose and hydroxypropylmethylcellulose. Tablets may also contain diluents such as lactose (monohydrate, spray-dried monohydrate, anhydrous), mannitol, xylitol, dextrose, sucrose, sorbitol, microcrystalline cellulose, starch and dibasic calcium phosphate dihydrate.

Tablets may also include surfactants such as sodium lauryl sulfate and polysorbate 80, and glidants such as silicon dioxide and talc. When present, surfactants may comprise from about 0.2 wt % to about 5 wt % of the tablet, and glidants may comprise from about 0.2 wt % to about 1 wt % of the tablet.

Tablets may also contain lubricants such as magnesium stearate, calcium stearate, zinc stearate, sodium stearyl fumarate, and mixtures of magnesium stearate with sodium lauryl sulfate. Lubricants may comprise from about 0.25 wt % to about 10 wt %, preferably from about 0.5 wt % to about 3 wt % of the tablet.

Tablet blends may be compressed directly or by roller compaction to form tablets. Tablet blends or portions of blends may alternatively be wet-, dry- or melt-granulated, melt congealed, or extruded before tableting. If desired, prior to blending, one or more of the components may be sized by screening or milling or both. The final dosage form may comprise one or more layers, and may be coated, uncoated or encapsulated. Exemplary tablets may contain up to about 80 wt % of API, from about 10 wt % to about 90 wt % of binder, from about 0 wt % to about 85 wt % of diluent, from about 2 wt % to about 10 wt % of disintegrant, and from about 0.25 wt % to about 10 wt % of lubricant. For a discussion of blending, granulation, milling, screening, tableting, coating as well as alternative techniques for preparing drug products, see A. R. Gennaro (ed.), *Remington: The Science and Practice of Pharmacy* (20th ed., 2000); H. A. Lieberman et al. (ed.), *Pharmaceutical Dosage Forms: Tablets*, Vol. 1-3 (2d ed., 1990); and D. K. Parikh & C. K. Parikh, *Handbook of Pharmaceutical Granulation Technology*, Vol. 81 (1997).

Consumable oral films for human or veterinary use are pliable water-soluble or water-swellable thin film dosage forms which may be rapidly dissolving or mucoadhesive. In addition to the API, a typical film includes one or more film-forming polymers, binders, humectants, plasticizers, stabilizers or emulsifiers, viscosity-modifying agents and solvents. Other film ingredients may include anti-oxidants, colorants, flavorants and flavor enhancers, preservatives, salivary stimulating agents, cooling agents, co-solvents (including oils), emollients, bulking agents, anti-foaming agents, surfactants and taste-masking agents. Some components of the formulation may perform more than one function.

In addition to dosing requirements, the amount of API in the film may depend on its solubility. If water soluble, the API would typically comprise from about 1 wt % to about 80 wt % of the non-solvent components (solutes) in the film, preferably from about 20 wt % to about 50 wt % of the solutes in the film. A less soluble API may comprise a greater proportion of the composition, typically up to about 88 wt % of the non-solvent components in the film.

The film-forming polymer may be selected from natural polysaccharides, proteins or synthetic hydrocolloids, and typically comprises from about 0.01 wt % to about 99 wt %, preferably from about 30 wt % to about 80 wt % of the film.

Film dosage forms are typically prepared by evaporative drying of thin aqueous films coated onto a peelable backing support or paper, which may carried out in a drying oven or tunnel (e.g., in a combined coating-drying apparatus), in lyophilization equipment, or in a vacuum oven.

Useful solid formulations for oral administration may include immediate release formulations and modified release formulations. Modified release formulations include delayed-, sustained-, pulsed-, controlled-, targeted- and programmed-release. For a general description of suitable modified release formulations, see U.S. Pat. No. 6,106,864. For details of other useful release technologies such as high energy dispersions and osmotic and coated particles, see Verma et al, *Pharmaceutical Technology On-line* (2001) 25(2):1-14.

The cocrystals of the present invention may also be administered directly into the blood stream, muscle or an internal organ of the subject. Suitable techniques for parenteral administration include intravenous, intraarterial, intraperitoneal, intrathecal, intraventricular, intraurethral, intrasternal, intracranial, intramuscular, intrasynovial, and subcutaneous administration. Suitable devices for parenteral administration include needle injectors, including microneedle injectors, needle-free injectors, and infusion devices.

Parenteral formulations are typically aqueous solutions which may contain excipients such as salts, carbohydrates and buffering agents (e.g., pH of from 3 to 9). For some applications, however, the cocrystals of the present invention may be more suitably formulated as a sterile non-aqueous solution or as a dried form to be used in conjunction with a suitable vehicle such as sterile, pyrogen-free water. The preparation of parenteral formulations under sterile conditions (e.g., by lyophilization) may be readily accomplished using standard pharmaceutical techniques.

The solubility of compounds which are used in the preparation of parenteral solutions may be increased through appropriate formulation techniques such as the incorporation of solubility-enhancing agents. Formulations for parenteral administration may be formulated to be immediate or modified release. Modified release formulations include delayed, sustained, pulsed, controlled, targeted and programmed release. Thus, the cocrystals of the present invention may be formulated as a suspension, a solid, a semi-solid or a thixotropic liquid for administration as an implanted depot providing modified release of the active compound. Examples of such formulations include drug-coated stents, and semi-solids or suspensions comprising drug-loaded poly (DL-lactic-coglycolic)acid (hereinafter sometimes to be abbreviated as "PGLA") microspheres.

The cocrystals of the present invention may also be administered topically, intradermally or transdermally to the skin or mucosa. Typical formulations for this purpose include gels, hydrogels, lotions, solutions, creams, ointments, dusting powders, dressings, foams, films, skin patches, wafers, implants, sponges, fibers, bandages and microemulsions. Liposomes may also be used. Typical carriers may include alcohol, water, mineral oil, liquid petrolatum, white petrolatum, glycerin, polyethylene glycol and propylene glycol. Topical formulations may also include penetration enhancers. See, e.g., Finnin and Morgan, *J. Pharm. Sci.* 88(10):955-958 (1999).

Other means of topical administration include delivery by electroporation, iontophoresis, phonophoresis, sonophoresis, microneedle or needle-free (e.g. Powderject™ and Bioject™) injection. Formulations for topical administration may be formulated to be immediate or modified release as described above.

The cocrystals of the present invention may also be administered intranasally or by inhalation, typically in the form of a dry powder, an aerosol spray or nasal drops. An inhaler may be used to administer the dry powder, which comprises the API alone, a powder blend of the API and a diluent such as lactose, or a mixed component particle that includes the API and a phospholipid such as phosphatidylcholine. For intranasal use, the powder may include a bioadhesive agent, e.g., chitosan or cyclodextrin. A pressurized container, pump, sprayer, atomizer or nebulizer, may be used to generate the aerosol spray from a solution or suspension comprising the API, one or more agents for dispersing, solubilizing or extending the release of the API (e.g., ethanol with or without water), one or more solvents (e.g., 1,1,1,2-tetrafluoroethane or 1,1,1,2,3,3,3-heptafluoropropane) which serve as a propellant, and an optional surfactant such as sorbitan trioleate, oleic acid, and an oligolactic acid. An atomizer using electrohydrodynamics may be used to produce a fine mist.

Prior to use in a dry powder or suspension formulation, the drug is usually comminuted to a particle size suitable for delivery by inhalation (typically 90% of the particles, based on volume, having a largest dimension less than 5 microns). This may be achieved by any appropriate size reduction method such as spiral jet milling, fluid bed jet milling, supercritical fluid processing, high pressure homogenization and spray drying.

Capsules, blisters and cartridges (made, for example, from gelatin or hydroxypropylmethyl cellulose) for use in an inhaler or insufflator may be formulated to contain a powder mixture of the active compound, a suitable powder base such as lactose and starch, and a performance modifier such as L-leucine, mannitol and magnesium stearate. The lactose may be anhydrous or monohydrated. Other suitable excipients include dextran, glucose, maltose, sorbitol, xylitol, fructose, sucrose and trehalose.

A suitable solution formulation for use in an atomizer using electrohydrodynamics to produce a fine mist may contain from about 1 µg to about 20 mg of the API per actuation, and the actuation volume may vary from about 1 µL to about 100 µL. A typical formulation may comprise one or more cocrystals of the present invention, propylene glycol, sterile water, ethanol and NaCl. Alternative solvents, which may be used instead of propylene glycol, include glycerol and polyethylene glycol.

Formulations for inhaled administration, intranasal administration, or both, may be formulated to be immediate or modified release using, for example, PGLA. Suitable flavors such as menthol and levomenthol, or sweeteners such as saccharin and sodium saccharin, may be added to formulations intended for inhaled/intranasal administration.

In the case of dry powder inhalers and aerosols, the dosage unit is determined by means of a valve that delivers a metered amount. Units are typically arranged to administer a metered dose or "puff" containing from about 10 µg to about 1000 µg of the API. The overall daily dose will typically range from about 100 µg to about 10 mg which may be administered in a single dose or, more usually, as divided doses throughout the day.

The cocrystals of the present invention may be administered rectally or vaginally, e.g., in the form of a suppository, pessary or enema. Cocoa butter is a traditional suppository base, but various alternatives may be used as appropriate. Formulations for rectal or vaginal administration may be formulated to be immediate or modified release as described above.

The cocrystals of the present invention may also be administered directly to the eye or ear, typically in the form of drops of a micronized suspension or solution in isotonic and pH-adjusted sterile saline. Other formulations suitable for ocular and aural administration include ointments, gels, biodegradable implants (e.g. absorbable gel sponges, collagen), non-biodegradable implants (e.g. silicone), wafers, lenses, particulate, or vesicular systems such as niosomes or liposomes. The formulation may include one or more polymers and a preservative such as benzalkonium chloride. Typical polymers include crossed-linked polyacrylic acid, polyvinylalcohol, hyaluronic acid, cellulosic polymers (e.g., hydroxypropylmethylcellulose, hydroxyethylcellulose, methyl cellulose) and heteropolysaccharide polymers (e.g., gelan gum). Such formulations may also be delivered by iontophoresis. Formulations for ocular or aural administration may be formulated to be immediate or modified release as described above.

To improve the solubility, dissolution rate, taste-masking, bioavailability or stability of the cocrystals of the present invention, the cocrystals of the present invention may be combined with soluble macromolecular entities such as cyclodextrin and its derivatives, and polyethylene glycol-containing polymers. For example, API-cyclodextrin complexes are generally useful for most dosage forms and routes of administration. Both inclusion and non-inclusion complexes may be used. As an alternative to direct complexation with the API, the cyclodextrin may be used as an auxiliary additive, i.e. as a carrier, diluent or solubilizer. Alpha-, beta- and gamma-cyclodextrins are commonly used for these purposes. See, e.g., WO 91/11172, WO 94/02518 and WO 98/55148.

As noted above, the cocrystals of the present invention may be combined with each other or with one or more other pharmaceutically active compounds to treat various diseases, disorders or conditions. In such cases, the active compounds may be combined in a single dosage form as described above or may be provided in the form of a kit which is suitable for coadministration of the compositions. The kit comprises (1) two or more different pharmaceutical compositions, at least one of which contains the cocrystals of the present invention; and (2) a device for separately retaining the two pharmaceutical compositions such as a divided bottle or a divided foil packet. An example of such a kit is the familiar blister pack used for the packaging of tablets or capsules. The kit is suitable for administering different types of dosage forms (e.g., oral and parenteral) or for administering different pharmaceutical compositions at separate dosing intervals or for titrating the different pharmaceutical compositions against one another. To assist with patient compliance, the kit typically comprises directions for administration, and may be provided with a memory aid.

For administration to human patients, the total daily dose of the cocrystals of the present invention is typically in the range of about 0.1 mg to about 3000 mg depending on the route of administration. For example, oral administration may require a total daily dose of from about 1 mg to about 3000 mg, while an intravenous dose may only require a total daily dose of from about 0.1 mg to about 300 mg. The total daily dose may be administered in single or divided doses and, at the physician's discretion, may fall outside of the typical ranges given above. Although these dosages are based on an average human subject having a weight of about 60 kg to about 70 kg, the physician will be able to determine the appropriate dose for a patient (e.g., an infant) whose weight falls outside of this weight range. The cocrystals of the present invention may show low toxity and be superior in the dissolution property and oral absorbability, and be useful as a material of a medicament (pharmaceutical composition or formulation).

As noted above, the cocrystals of the present invention may be used to treat diseases, disorders or conditions for which inhibition of BTK is indicated. Such diseases, disorders or conditions generally relate to any unhealthy or abnormal state in a subject for which the inhibition of BTK provides a therapeutic benefit. More particularly, such diseases, disorders or conditions may involve the immune system and inflammation, including Type I hypersensitivity (allergic) reactions (allergic rhinitis, allergic asthma and atopic dermatitis); autoimmune diseases (rheumatoid arthritis, multiple sclerosis, systemic lupus erythematosus, psoriasis, lupus nephritis, immune thrombocytopenic purpura, Sjögren's syndrome, ankylopoietic spondylarthritis and Behcet's disease); inflammatory bowel disease; inflammation of the lung (chronic obstructive pulmonary disease), atherosclerosis, thrombosis and myocardial infarction. The cocrystals of the present invention may also be used to treat diseases, disorders or conditions related to abnormal cell proliferation, including hematological malignancies such as acute myeloid leukemia, B-cell chronic lymphocytic leukemia, B-cell lymphoma (e.g., mantle cell lymphoma), T-cell lymphoma (e.g., peripheral T-cell lymphoma) and multiple myeloma, as well as epithelial cancers (i.e., carcinomas) such as lung cancer (small cell lung cancer and non-small cell lung cancer), pancreatic cancer and colorectal cancer.

In addition to the hematological malignancies and epithelial cancers noted above, the cocrystals of the present invention may also be used to treat other types of cancer, including leukemia (chronic myeloid leukemia and chronic lymphocytic leukemia); breast cancer, genitourinary cancer, skin cancer, bone cancer, prostate cancer and liver cancer; brain cancer; cancer of the larynx, gall bladder, rectum, parathyroid, thyroid, adrenal, neural tissue, bladder, head, neck, stomach, bronchi and kidneys; basal cell carcinoma, squamous cell carcinoma, metastatic skin carcinoma, osteosarcoma, Ewing's sarcoma, reticulum cell sarcoma and Kaposi's sarcoma; myeloma, giant cell tumor, islet cell tumor, acute and chronic lymphocytic and granulocytic tumors, hairy-cell tumor, adenoma, medullary carcinoma, pheochromocytoma, mucosal neuromas, intestinal ganglioneuromas, hyperplastic corneal nerve tumor, marfanoid habitus tumor, Wilms' tumor, seminoma, ovarian tumor, leiomyomater tumor, cervical dysplasia, neuroblastoma, retinoblastoma, myelodysplastic syndrome, rhabdomyosarcoma, astrocytoma, non-Hodgkin's lymphoma, malignant hypercalcemia, polycythermia vera, glandular cancer, glioblastoma multiforma, glioma, lymphomas and malignant melanomas, among others.

In addition to cancer, the cocrystals of the present invention may also be used to treat other diseases, disorders or conditions related to abnormal cell proliferation, including non-malignant proliferative diseases such as benign prostatic hypertrophy, restinosis, hyperplasia, synovial proliferation disorder, idiopathic plasmacytic lymphadenopathy, retinopathy or other neovascular disorders of the eye, among others.

The cocrystals of the present invention may also be used to treat autoimmune diseases, disorders or conditions in addition to those listed above. Such diseases, disorders or conditions include Crohns disease, dermatomyositis, diabetes mellitus type 1, Goodpasture's syndrome, Graves' disease, Guillain-Barré syndrome, Hashimoto's disease, mixed connective tissue damage, myasthenia gravis, narcolepsy, pemphigus vulgaris, pernicious anemia, polymyositis, primary biliary cirrhosis, temporal arteritis, ulcerative colitis, vasculitis and Wegener's granulomatosis, among others.

The cocrystals of the present invention may be used to treat inflammatory diseases, disorders or conditions including asthma, chronic inflammation, chronic prostatitis, glomerulonephritis, hypersensitivities, inflammatory bowel diseases (ulcerative colitis in addition to Crohn's disease), pelvic inflammatory disease, reperfusion injury, transplant rejection, vasculitis and systemic inflammatory response syndrome.

The cocrystals of the present invention may also be used to treat specific diseases or conditions that may fall within one or more general disorders described above, including arthritis. In addition to rheumatoid arthritis, Sjögren's syndrome, systemic lupus erythematosus, SLE in children and adolescents, the cocrystals of the present invention may also be used to treat other arthritis diseases, including ankylopoietic spondylarthritis, avascular necrosis, Behcet's disease, bursitis, calcium pyrophosphate dihydrate crystal deposition disease (pseudo gout), carpal tunnel syndrome, Ehlers-Danlos syndrome, fibromyalgia, Fifth disease, giant cell arteritis, gout, juvenile dermatomyositis, juvenile rheumatoid arthritis, juvenile spondyloarthropathy, Lyme disease, Marfan syndrome, myositis, osteoarthritis, osteogenesis imperfect, osteoporosis, Paget's disease, psoriatic arthritis, Raynaud's phenomenon, reactive arthritis, reflex sympathetic dystrophy syndrome, scleroderma, spinal stenosis, Still's disease and tendinitis, among others.

The cocrystals of the present invention may be combined with one or more other pharmacologically active compounds or therapies for the treatment of one or more diseases, disorders or conditions for which BTK is indicated, including those involving the immune system, inflammation and abnormal cell proliferation. For example, the cocrystals of the present invention may be administered simultaneously, sequentially or separately in combination with one or more compounds or therapies for treating arthritis, including rheumatoid arthritis and osteoarthritis, or for treating cancer, including hematological malignancies such as acute myeloid leukemia, B-cell chronic lymphocytic leukemia, B-cell lymphoma, T-cell lymphoma and multiple myeloma, and carcinomas such as lung cancer, pancreatic cancer and colorectal cancer. Such combinations may offer significant therapeutic advantages, including fewer side effects, improved ability to treat undeserved patient populations or synergistic activity.

For example, when used to treat arthritis, the cocrystals of the present invention may be combined with one or more nonsteroidal anti-inflammatory drugs (NSAIDs), analgesics, corticosteroids, biological response modifiers, and protein-A immunoadsorption therapy. Alternatively or additionally, when treating rheumatoid arthritis, the cocrystals of the present invention may be combined with one or more disease modifying antirheumatic drugs (DMARDs), and when treating osteoarthritis, the cocrystals of the present invention may be combined with one or more osteoporosis agents.

Representative NSAIDs include apazone, aspirin, celecoxib, diclofenac (with and without misoprostol), diflunisal, etodolac, fenoprofen, flurbiprofen, ibuprofen, indomethacin, ketoprofen, meclofenamate sodium, mefenamic acid, meloxicam, nabumetone, naproxen, oxaprozin, phenylbutazone, piroxicam, choline and magnesium salicylates, salsalate and sulindac. Representative analgesics include acetaminophen and morphine sulfate, as well as codeine, hydrocodone, oxycodone, propoxyphene and tramadol, all with or without acetaminophen. Representative corticosteroids include betamethasone, cortisone acetate, dexamethasone, hydrocortisone, methylprednisolone, predonisolone and prednisone. Representative biological response modifiers include TNF-α inhibitors such as adalimumab, etanercept and infliximab; selective B-cell inhibitors such as rituximab; IL-1 inhibitors such as anakinra; and selective costimulation modulators such as abatacept.

Representative DMARDs include auranofin (oral gold), azathioprine, chlorambucil, cyclophosamide, cyclosporine, sodium aurothiomalate (injectable gold), hydroxychloroquine, leflunomide, methotrexate, minocycline, mycophenolate mofetil, penicillamine, sulfasalazine and JAK3 inhibitors (e.g., tofacitinib). Representative osteoporosis agents include bisphosphonates such as alendronate, ibandronate, risedronate and zoledronic acid; selective estrogen receptor modulators such as droloxifene, lasofoxifene and raloxifene; hormones such as calcitonin, estrogens and parathyroid hormone; and immunosuppressant agents such as azathioprine, cyclosporine and rapamycin.

Particularly useful combinations for treating rheumatoid arthritis include a combination of the cocrystals of the present invention and methotrexate; a combination of the cocrystals of the present invention and one or more biological response modifiers such as leflunomide, etanercept, adalimumab and infliximab; and a combination of the cocrystals of the present invention, methotrexate and one or more biological response modifiers such as leflunomide, etanercept, adalimumab and infliximab.

For the treatment of thrombus and restenosis, the cocrystals of the present invention may be combined with one or more cardiovascular agents such as calcium channel blockers, statins, fibrates, beta-blockers, ACE inhibitors and platelet aggregation inhibitors.

The cocrystals of the present invention may also be combined with one or more compounds or therapies for treating cancer. These include chemotherapeutic agents (i.e., cytotoxic or antineoplastic agents) such as alkylating agents, antibiotics, antimetabolic agents, plant-derived agents and topoisomerase inhibitors, as well as molecularly targeted drugs which block the growth and spread of cancer by interfering with specific molecules involved in tumor growth and progression. Molecularly targeted drugs include both small molecules and biologics.

Representative alkylating agents include bischloroethylamines (nitrogen mustards, e.g., chlorambucil, cyclophosphamide, ifosfamide, mechlorethamine, melphalan and uracil mustard); aziridines (e.g., thiotepa); alkyl alkane sulfonates (e.g., busulfan); nitrosoureas (e.g., carmustine, lomustine and streptozocin); nonclassical alkylating agents (e.g., altretamine, dacarbazine and procarbazine); and platinum compounds (e.g., carboplatin, cisplatin, nedaplatin, oxaliplatin, satraplatin and triplatin tetranitrate).

Representative antibiotic agents include anthracyclines (e.g., aclarubicin, amrubicin, daunorubicin, doxorubicin, epirubicin, idarubicin, pirarubicin, valrubicin and zorubicin); anthracenediones (e.g., mitoxantrone and pixantrone); and *streptomyces* (e.g., actinomycin, bleomycin, dactinomycin, mitomycin C and plicamycin).

Representative antimetabolic agents include dihydrofolate reductase inhibitors (e.g., aminopterin, methotrexate and pemetrexed); thymidylate synthase inhibitors (e.g., raltitrexed and pemetrexed); folinic acids (e.g., leucovorin); adenosine deaminase inhibitors (e.g., pentostatin); halogenated/ribonucleotide reductase inhibitors (e.g., cladribine, clofarabine and fludarabine); thiopurines (e.g., thioguanine and mercaptopurine); thymidylate synthase inhibitors (e.g., fluorouracil, capecitabine, tegafur, carmofur and floxuridine); DNA polymerase inhibitors (e.g., cytarabine); ribonucleotide reductase inhibitors (e.g., gemcitabine); hypomethylating agents (e.g., azacitidine and decitabine); ribonucleotide reductase inhibitors (e.g., hydroxyurea); and asparagine depleters (e.g., asparaginase).

Representative plant-derived agents include *vinca* alkaloids (e.g., vincristine, vinblastine, vindesine, vinzolidine and vinorelbine), podophyllotoxins (e.g., etoposide and teniposide), and taxanes (e.g., docetaxel, larotaxel, ortataxel, paclitaxel and tesetaxel).

Representative type I topoisomerase inhibitors include camptothecins such as belotecan, irinotecan, rubitecan and topotecan. Representative type II topoisomerase inhibitors include amsacrine, etoposide, etoposide phosphate and teniposide, which are derivatives of epipodophyllotoxins.

Molecular targeted drugs include biologic agents such as cytokines and other immune-regulating agents. Useful cytokines include interleukin-2 (IL-2, aldesleukin), interleukin 4 (IL-4), interleukin 12 (IL-12) and interferon, which includes more than 23 related subtypes. Other cytokines include granulocyte colony stimulating factors (CSF) (e.g., filgrastim) and granulocyte macrophage colony stimulating factors (GM-CSF or CSF2) (e.g., sargramostim, namilumab). Other immuno-modulating agents include *bacillus* Calmette-Guerin, levamisole and octreotide; monoclonal antibodies against tumor antigens such as trastuzumab and rituximab; and cancer vaccines, which induce an immune response to tumors.

In addition, molecularly targeted drugs that interfere with specific molecules involved in tumor growth and progression include inhibitors of epidermal growth factor (EGF), transforming growth factor-alpha ($TGF_\alpha$), $TGF_\beta$, heregulin, insulin-like growth factor (IGF), fibroblast growth factor (FGF), keratinocyte growth factor (KGF), colony stimulating factor (CSF), erythropoietin (EPO), interleukin-2 (IL-2), nerve growth factor (NGF), platelet-derived growth factor (PDGF), hepatocyte growth factor (HGF), vascular endothelial growth factor (VEGF), angiopoietin, epidermal growth factor receptor (EGFR), human epidermal growth factor receptor 2 (HER2), HERO, insulin-like growth factor 1 receptor (IGF1R), IGF2R, fibroblast growth factor 1 receptor (FGF1R), FGF2R, FGF3R, FGF4R, vascular endothelial growth factor receptor (VEGFR), tyrosine kinase with immunoglobulin-like and epidermal growth factor-like domains 2 (Tie-2), platelet-derived growth factor receptor (PDGFR), Abl, Bcr-Abl, Raf, FMS-like tyrosine kinase 3 (FLT3), c-Kit, Src, protein kinase c (PKC), tropomyosin receptor kinase (Trk), Ret, mammalian target of rapamycin (mTOR), Aurora kinase, polo-like kinase (PLK), mitogen activated protein kinase (MAPK), mesenchymal-epithelial transition factor (c-MET), cyclin-dependant kinase (CDK), Akt, extracellular signal-regulated kinases (ERK), poly (ADP) ribose polymerase (PARP), and the like.

Specific molecularly targeted drugs include selective estrogen receptor modulators such as tamoxifen, toremifene, fulvestrant and raloxifene; antiandrogens such as bicalutamide, nilutamide, megestrol and flutamide; and aromatase inhibitors such as exemestane, anastrozole and letrozole. Other specific molecularly targeted drugs include agents which inhibit signal transduction, such as imatinib, dasatinib, nilotinib, trastuzumab, gefitinib, erlotinib, cetuximab, lapatinib, panitumumab and temsirolimus; agents that induce apoptosis, such as bortezomib; agents that block angiogenesis, such as bevacizumab, sorafenib and sunitinib; agents that help the immune system destroy cancer cells, such as rituximab and alemtuzumab; and monoclonal antibodies which deliver toxic molecules to cancer cells, such as gemtuzumab ozogamicin, tositumomab, 131I-tositumomab and ibritumomab tiuxetan.

The cocrystals of the present invention can also be used for the treatment of allergic conjunctivitis, uveitis, blepharitis, keratitis, optic neuritis, Graves ophthalmopathy, scleritis, ocular histoplasmosis syndrome, ocular cicatricial pemphigoid, diabetic retinopathy or cancer-related autoimmune retinopathy.

EXAMPLES

While the present invention is explained in more detail in the following by referring to Production Examples and the like, the present invention is not limited by the following Production Examples and the like, and can be performed by adding appropriate modifications within the range that can conform to the above-mentioned and the below-mentioned gist, all of which are encompassed in the technical scope of the present invention.

The "room temperature" described below generally means about 10° C.-about 35° C.

The ratios and percentages indicated for mixed solvents mean volume ratio and % by volume, unless otherwise specified.

The percentages shown as the yield are mol %.

Unless otherwise specified, the percentages other than for the solvent and yield are wt %.

Abbreviations used in Production Examples and the like mean the following.

DMSO: dimethyl sulfoxide
TGA: thermogravimetric analysis
DSC: differential scanning calorimetry
UPLC: ultrahigh performance liquid chromatography
LC: liquid chromatography
MS/MS: tandem mass spectrometry Melting points were measured under the following conditions. The melting point here is the temperature at the intersection with the tangent line of the inflection point (point of maximum gradient) of the DSC curve shown up to the melting process from the baseline on the melting start side to the peak top in the measurement results, namely, the melting reaction starting point temperature (onset temperature).

measuring apparatus: METTLER TOLEDO (TGA/DSC1&DSC1)
measurement conditions
   temperature rise rate: 5° C./min
   atmosphere: $N_2$ Measurement of powder X-ray diffraction was performed under the following conditions.
measuring apparatus: RIGAKU Ultima IV
measurement conditions
   tube voltage: 40 kV
   tube current: 50 mA
   scan speed: 6°/min
   scan angle (2θ): 2-35°

Production Example 1: Production of Cocrystals of Compound (A) and Gentisic Acid To compound (A) (700 mg) in an eggplant flask (100 mL) was added a saturated acetonitrile solution (35 mL) of gentisic acid, the eggplant flask was sealed with a glass stopper under air atmosphere, and the suspension was stirred with a magnetic stirrer at 450 rpm at room temperature for 5 days. The crystals in the suspension were collected by filtration, washed 3 times with acetonitrile, and suction dried to give the object cocrystals (965 mg, yield 96.0%) as an off-white powder. The melting point of the cocrystals measured under the above-mentioned conditions was 226° C. The 2θ and d values of the powder X-ray diffraction peaks of the cocrystals measured under the above-mentioned conditions are shown in Table 1.

TABLE 1

| powder X-ray diffraction peaks of cocrystals of compound (A) and gentisic acid | |
|---|---|
| 2θ (°) | d value (Å) |
| 6.680 | 13.2212 |
| 8.020 | 11.0149 |
| 8.800 | 10.0403 |
| 14.380 | 6.1544 |
| 14.860 | 5.9566 |
| 16.740 | 5.2917 |
| 18.900 | 4.6915 |
| 24.460 | 3.6362 |
| 27.100 | 3.2877 |

The content of gentisic acid in the cocrystal measured by UPLC under the following conditions was 1.007 mol per 1 mol of compound (A).
system: Aquity UPLC H-Class (Waters)
detector: 214 nm
separation column: YMC Triart-C18 1.9 μm, 2.0×75 mm (YMC Co., Ltd.)
column temperature: 40° C.
mobile phase A: 20 mmol/L sodium hydrogen carbonate buffer (pH 2.5)
mobile phase B: acetonitrile
flow: 0.4 mL/min
analysis time: 20.0 min
injection volume: 2.5 μL
solvent: water/acetonitrile (1:1)

TABLE 2

| gradient | |
|---|---|
| time (min) | concentration (%) of mobile phase B |
| 0 | 1 |
| 1.5 | 1 |
| 6.5 | 75 |
| 10 | 75 |
| 10.01 | 1 |
| 20 | 1 |

The base pKa of the compound (A) and the acid pKa of the gentisic acid were measured using a Sirius T3 titrator manufactured by Sirius. The base pKa means an acid dissociation constant from the protonated state, and the acid pKa means the acid dissociation constant of the acid itself.

As a result, the base pKa of compound (A) was not more than 2 (outside the measurement range of the above-mentioned titrator), and an accurate value could not be measured. The acid pKa of gentisic acid was 3.23. The "base pKa of compound (A)—acid pKa of gentisic acid" was less than 0, and proton transfer is impossible between compound (A) and gentisic acid. Likewise, since the acid pKa of other carboxylic acids used in other Production Examples is considered to be in the range of 3 to 5, proton transfer between compound (A) and other carboxylic acid is also considered to be impossible in other Production Examples.

In addition, it was confirmed by IR spectrum of the cocrystals obtained in Production Example 1 that the peak of carboxy group of gentisic acid was maintained in the cocrystal. From this result, it was also confirmed that the proton was not transferred between compound (A) and gentisic acid in the cocrystal.

In addition, since no weight loss was observed in thermal analysis, it was confirmed that the cocrystal obtained in Production Example 1 was a nonhydrate.

Figure 2:
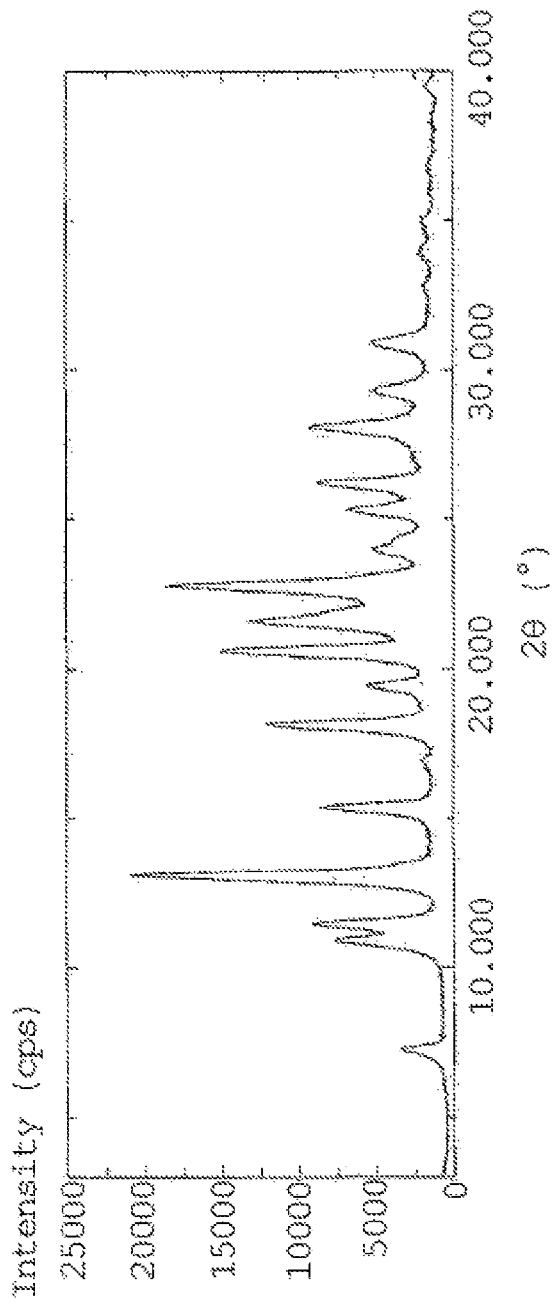
FIG. 2 is a powder X-ray diffraction chart of compound (A).
Figure 3:
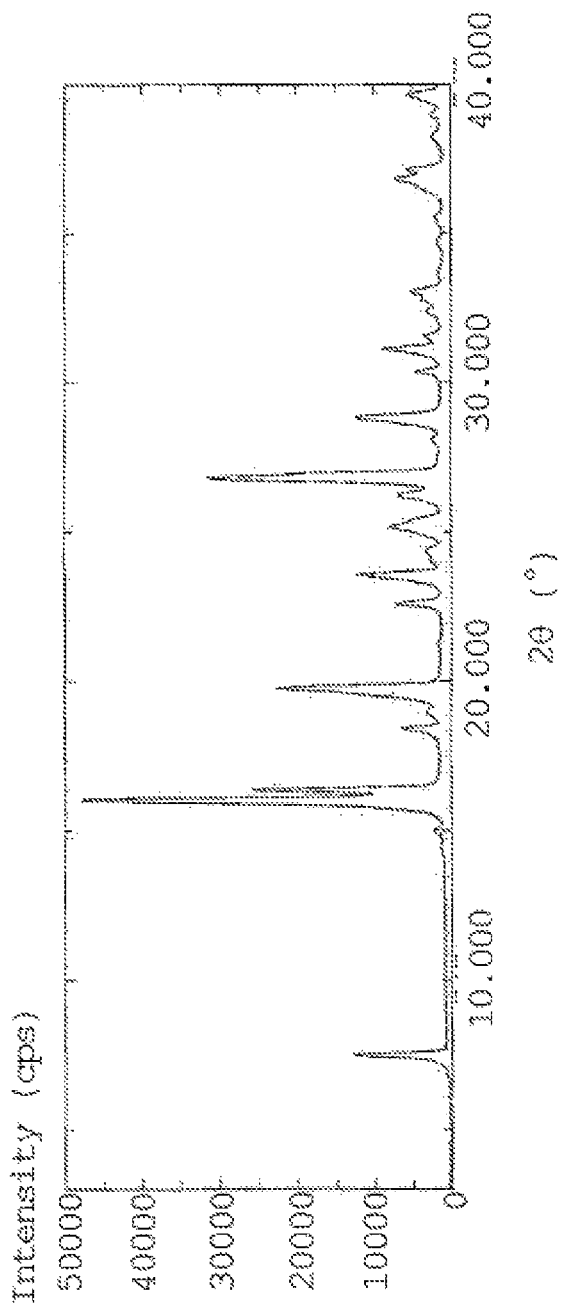
FIG. 3 is a powder X-ray diffraction chart of gentisic acid.

Production Example 2: Production of Cocrystals of Compound (A) and Gentisic Acid Gentisic acid (about 4.5 g) was suspended in acetonitrile (60 mL) and the suspension was stirred with a magnetic stirrer at room temperature for less than 1 hr. Undissolved crystals were filtrated off and a saturated solution was prepared. Compound (A) (1.0 g) was suspended in the saturated solution (50 mL), and the suspension was stirred with a magnetic stirrer at room temperature for 5 days, and ultrasonicated for 3 min. The crystals were collected by filtration at room temperature, and the obtained wet crystals were dried under reduced pressure to give the object cocrystals (0.71 g, yield 49.3%, molar ratio of compound (A):gentisic acid=1:1) as an off-white powder. The melting point of the cocrystals measured under the above-mentioned conditions was 224° C. The difference in the melting points of the cocrystals of Production Examples 1 and 2 is considered to be attributable to a measurement error. Powder X-ray diffraction of the obtained cocrystals was measured under the above-mentioned conditions to find a powder X-ray diffraction pattern having characteristic peaks at lattice spacings (d) of about 12.92, 10.86, 9.87, 6.11, 5.94, 5.26, 4.66, 3.62 and 3.26 angstroms. The 2θ and d values of the powder X-ray diffraction peaks of the cocrystals measured under the above-mentioned conditions are shown in Table 3. In addition, a powder X-ray diffraction chart of the cocrystals obtained by measuring under the above-mentioned conditions is shown in FIG. 1, a powder X-ray diffraction chart of compound (A) is shown in FIG. 2, and a powder X-ray diffraction chart of gentisic acid is shown in FIG. 3. Since no weight loss was observed in thermal analysis, it was confirmed that the cocrystal was a nonhydrate.

TABLE 3

| 2θ (°) | d value (Å) |
| --- | --- |
| 6.84 | 12.92 |
| 8.13 | 10.86 |
| 8.95 | 9.87 |
| 14.49 | 6.11 |
| 14.90 | 5.94 |
| 16.85 | 5.26 |
| 19.04 | 4.66 |
| 24.59 | 3.62 |
| 27.32 | 3.26 | powder X-ray diffraction peaks of cocrystals of compound (A) and gentisic acid

Production Example 3: Production of Cocrystals of Compound (A) and Gentisic Acid A solution of gentisic acid (2.28 g) in a mixed solvent (9 mL, isopropyl alcohol amount 50%) of isopropyl alcohol and water (concentration of gentisic acid: 1.64 mol/L) was added dropwise to a 0.25 mol/L aqueous sodium hydroxide solution of compound (A) (1.0 g) (15 mL, concentration of compound (A) 0.190 mol/L) at room temperature. The concentration of gentisic acid in the mixed solution after dropwise addition was 0.592 mol/L. The cocrystals (1 mg) obtained in Production Example 2 were added as seed crystals, and the mixture was stirred with a magnetic stirrer at room temperature for 4 hr. Crystals were collected by filtration, and washed twice with acetone (5 mL) to give wet crystals. The obtained wet crystals were dried under reduced pressure to give the object cocrystals (1.42 g, yield 98.7%, molar ratio of compound (A):gentisic acid=1:1) as an off-white powder. Powder X-ray diffraction of the obtained cocrystals was measured under the above-mentioned conditions to find a powder X-ray diffraction pattern having characteristic peaks at lattice spacings (d) of about 13.13, 11.01, 10.05, 6.17, 5.98, 5.31, 4.68, 3.62 and 3.28 angstroms. The 2θ and d values of the powder X-ray diffraction peaks of the cocrystals measured under the above-mentioned conditions are shown in Table 4. Since no weight loss was observed in thermal analysis, it was confirmed that the cocrystal was a nonhydrate.

TABLE 4

| 2θ (°) | d value (Å) |
| --- | --- |
| 6.73 | 13.13 |
| 8.02 | 11.01 |
| 8.80 | 10.05 |
| 14.34 | 6.17 |
| 14.80 | 5.98 |
| 16.69 | 5.31 |
| 18.95 | 4.68 |
| 24.58 | 3.62 |
| 27.13 | 3.28 | powder X-ray diffraction peaks of cocrystals of compound (A) and gentisic acid

Production Example 4: Production of Cocrystals of Compound (A) and Gentisic Acid A solution of gentisic acid (40.35 g) in a mixed solvent (161 mL, isopropyl alcohol amount 50%) of isopropyl alcohol and water was filtrated to remove dust, and then, the container used was washed with a mixed solvent of isopropyl alcohol and water (9 mL, isopropyl alcohol amount 50%), and the washing liquid was filtered. The filtrate and the washing liquid were combined to give a solution of gentisic acid. A solution (345 mL) of compound (A) (23.0 g) in 0.25 mol/L aqueous sodium hydroxide was filtrated to remove dust, the container used was washed with a mixed solvent (23 mL, isopropyl alcohol amount 50%) of isopropyl alcohol and water, and the washing was filtered. The filtrate and the washing were combined to give a solution of compound (A). The solution of gentisic acid obtained as mentioned above was added dropwise to the solution of compound (A). The solution of gentisic acid was added dropwise, the container used was washed with a mixed solvent (9 mL, isopropyl alcohol amount 50%) of isopropyl alcohol and water, and the washing liquid was added dropwise. The concentration of gentisic acid in the mixed solution after dropwise addition was 0.479 mol/L. The cocrystals (23 mg) obtained in Production Example 3 were added as seed crystals, and the mixture was stirred using an impeller (three-one motor) at 300 rpm at room temperature for 2 days. The crystals were collected by filtration, and washed with a mixed solvent (115 mL, isopropyl alcohol amount 20%) of isopropyl alcohol and water to give wet crystals. The obtained wet crystals were dried under reduced pressure to give the object cocrystals (31.9 g, yield 96.4%, molar ratio of compound (A):gentisic acid=1:1) as an off-white powder. Powder X-ray diffraction of the obtained cocrystals was measured under the above-mentioned conditions to find a powder X-ray diffraction pattern having characteristic peaks at lattice spacings (d) of about 13.09, 10.95, 9.98, 6.15, 5.98, 5.29, 4.68, 3.63 and 3.27 angstroms. The 2θ and d values of the powder X-ray diffraction peaks of the cocrystals measured under the above-mentioned conditions are shown in Table 5. Since no weight loss was observed in thermal analysis, it was confirmed that the cocrystal was a nonhydrate.

TABLE 5 powder X-ray diffraction peaks of cocrystals of compound (A) and gentisic acid

| 2θ (°) | d value (Å) |
|---|---|
| 6.75 | 13.09 |
| 8.07 | 10.95 |
| 8.86 | 9.98 |
| 14.39 | 6.15 |
| 14.81 | 5.98 |
| 16.75 | 5.29 |
| 18.97 | 4.68 |
| 24.48 | 3.63 |
| 27.22 | 3.27 |

Production Example 5: Production of Cocrystals of Compound (A) and Gentisic Acid A solution of gentisic acid (2.28 g) in a mixed solvent of isopropyl alcohol and water (9 mL, isopropyl alcohol amount 50%) (concentration of gentisic acid 1.64 mol/L) was added dropwise to a solution of compound (A) (1.0 g) in 0.25 mol/L aqueous sodium hydroxide (15 mL, concentration of compound (A) 0.190 mol/L) at room temperature. The concentration of gentisic acid in the mixed solution after dropwise addition was 0.592 mol/L. The cocrystals (1 mg) obtained in Production Example 3 were added as seed crystals, and the mixture was stirred using a magnetic stirrer at room temperature for 2 hr. The crystals were collected by filtration, and washed with a mixed solvent (5 mL, isopropyl alcohol amount 20%) of isopropyl alcohol and water and then with acetone (5 mL) to give wet crystals. The obtained wet crystals were dried under reduced pressure to give the object cocrystals (1.41 g, yield 98.0%, molar ratio of compound (A):gentisic acid=1:1) as an off-white powder. Powder X-ray diffraction of the obtained cocrystals was measured under the above-mentioned conditions to find a powder X-ray diffraction pattern having characteristic peaks at lattice spacings (d) of about 13.05, 10.92, 9.96, 6.16, 5.96, 5.29, 4.67, 3.64 and 3.28 angstroms. The 2θ and d values of the powder X-ray diffraction peaks of the cocrystals measured under the above-mentioned conditions are shown in Table 6. Since no weight loss was observed in thermal analysis, it was confirmed that the cocrystal was a nonhydrate.

TABLE 6 powder X-ray diffraction peaks of cocrystals of compound (A) and gentisic acid

| 2θ (°) | d value (Å) |
|---|---|
| 6.67 | 13.05 |
| 8.09 | 10.92 |
| 8.85 | 9.98 |
| 14.37 | 6.16 |
| 14.85 | 5.96 |
| 16.74 | 5.29 |
| 19.01 | 4.67 |

TABLE 6-continued powder X-ray diffraction peaks of cocrystals of compound (A) and gentisic acid

| 2θ (°) | d value (Å) |
|---|---|
| 24.47 | 3.64 |
| 27.19 | 3.28 |

Production Example 6: Production of Cocrystals of Compound (A) and Gentisic Acid A solution of gentisic acid (1.75 g) in a mixed solvent (7 mL, isopropyl alcohol amount 50%) of isopropyl alcohol and water (concentration of gentisic acid 1.63 mol/L) was added dropwise to a solution of compound (A) (1.0 g) in 0.25 mol/L aqueous sodium hydroxide (15 mL, concentration of compound (A) 0.190 mol/L) at room temperature. The concentration of gentisic acid in the mixed solution after dropwise addition was 0.495 mol/L. The cocrystals (1 mg) obtained in Production Example 3 were added as seed crystals, and the mixture was stirred with a magnetic stirrer at room temperature for 2.5 hr. The crystals were collected by filtration, and washed with a mixed solvent (5 mL, isopropyl alcohol amount 20%) of isopropyl alcohol and water to give wet crystals. The obtained wet crystals were dried under reduced pressure to give the object cocrystals (1.42 g, yield 98.7%, molar ratio of compound (A):gentisic acid=1:1) as an off-white powder. Powder X-ray diffraction of the obtained cocrystals was measured under the above-mentioned conditions to find a powder X-ray diffraction pattern having characteristic peaks at lattice spacings (d) of about 13.09, 10.95, 10.01, 6.14, 5.98, 5.29, 4.67, 3.65 and 3.28 angstroms. The 2θ and d values of the powder X-ray diffraction peaks of the cocrystals measured under the above-mentioned conditions are shown in Table 7. Since no weight loss was observed in thermal analysis, it was confirmed that the cocrystal was a nonhydrate.

TABLE 7 powder X-ray diffraction peaks of cocrystals of compound (A) and gentisic acid

| 2θ (°) | d value (Å) |
|---|---|
| 6.75 | 13.09 |
| 8.07 | 10.95 |
| 8.83 | 10.01 |
| 14.41 | 6.14 |
| 14.81 | 5.98 |
| 16.73 | 5.29 |
| 18.98 | 4.67 |
| 24.40 | 3.65 |
| 27.18 | 3.28 |

Production Example 7: Production of Cocrystals of Compound (A) and Gentisic Acid A solution of gentisic acid (1.32 g) in a mixed solvent (5 mL, isopropyl alcohol amount 50%) of isopropyl alcohol and water (concentration of gentisic acid 1.71 mol/L) was added dropwise to a solution of compound (A) (1.0 g) in 0.25 mol/L aqueous sodium hydroxide (15 mL) and a mixed solvent (1 mL) of isopropyl alcohol and water (isopropyl alcohol amount 50%) at room temperature. After dropwise addition, the container used for the dropwise addition was washed with a mixed solvent (1 mL) of isopropyl alcohol and water (isopropyl alcohol amount 50%), and the washing liquid was added dropwise. The concentration of gentisic acid in the mixed solution after dropwise addition was 0.388 mol/L. Then, the cocrystal (1 mg) obtained in Production Example 3 were added as seed crystals, and the mixture was stirred using an impeller (three-one motor) at room temperature for one day. The crystals were collected by filtration, and washed with a mixed solvent (5 mL) of isopropyl alcohol and water (isopropyl alcohol amount 20%) to give wet crystals. The obtained wet crystals were dried under reduced pressure to give the object cocrystals (1.39 g, yield 96.9%, molar ratio of compound (A):gentisic acid=1:1) as an off-white powder. Powder X-ray diffraction of the obtained cocrystals was measured under the above-mentioned conditions to find a powder X-ray diffraction pattern having characteristic peaks at lattice spacings (d) of about 12.94, 10.85, 9.90, 6.12, 5.94, 5.28, 4.66, 3.63 and 3.28 angstroms. The 2θ and d values of the powder X-ray diffraction peaks of the cocrystals measured under the above-mentioned conditions are shown in Table 8. Since no weight loss was observed in thermal analysis, it was confirmed that the cocrystal was a nonhydrate.

TABLE 8 powder X-ray diffraction peaks of cocrystals of compound (A) and gentisic acid

| 2θ (°) | d value (Å) |
|---|---|
| 6.83 | 12.94 |
| 8.14 | 10.85 |
| 8.92 | 9.90 |
| 14.46 | 6.12 |
| 14.90 | 5.94 |
| 16.78 | 5.28 |
| 19.04 | 4.66 |
| 24.51 | 3.63 |
| 27.20 | 3.28 |

Production Example 8: Production of Cocrystals of Compound (A) and Gentisic Acid (Pulverized Product)

A solution of gentisic acid (52.64 g) in a mixed solvent (200 mL) of isopropyl alcohol and water (isopropyl alcohol amount 50%) was filtrated to remove dust, the container used was washed with a mixed solvent (16 mL) of isopropyl alcohol and water (isopropyl alcohol amount 50%), and the washing was filtered. The filtrate and the washing were combined to give a solution of gentisic acid. A solution (600 mL) of compound (A) (40.0 g) in 0.25 mol/L aqueous sodium hydroxide was filtrated to remove dust, and the container used was washed with a mixed solvent (40 mL) of isopropyl alcohol and water (isopropyl alcohol amount 50%), and the washing was filtered. The filtrate and the washing were combined to give a solution of compound (A). The solution of gentisic acid obtained as mentioned above was added dropwise to the solution of compound (A). After the solution of gentisic acid was added dropwise, the container used was washed with a mixed solvent (16 mL, isopropyl alcohol amount 50%) of isopropyl alcohol and water, and the washing liquid was added dropwise. The concentration of gentisic acid in the mixed solution after dropwise addition was 0.392 mol/L. The cocrystals (40 mg) obtained in Production Example 3 were added as seed crystals, and the mixture was stirred using a three-one motor at 300 rpm at room temperature for one day. The crystals were collected by filtration, and washed with a mixed solvent (200 mL, isopropyl alcohol amount 20%) of isopropyl alcohol and water to give wet crystals. The obtained wet crystals were dried under reduced pressure to give the object cocrystals (56.35 g, yield 97.9%, molar ratio of compound (A):gentisic acid=1:1) as an off-white powder. The obtained powder (50 g) was pulverized in a jet mill to give a pulverized product (43.26 g, yield 86.5%). Powder X-ray diffraction of the obtained cocrystals (pulverized product) was measured under the above-mentioned conditions to find a powder X-ray diffraction pattern having characteristic peaks at lattice spacings (d) of about 12.86, 10.82, 9.89, 6.10, 5.92, 5.26, 4.64, 3.63 and 3.27 angstroms. The 2θ and d values of the powder X-ray diffraction peaks of the cocrystals (pulverized product) measured under the above-mentioned conditions are shown in Table 9. Since no weight loss was observed in thermal analysis, it was confirmed that the cocrystal was a nonhydrate.

TABLE 9 powder X-ray diffraction peaks of cocrystals of compound (A) and gentisic acid

| 2θ (°) | d value (Å) |
|---|---|
| 6.87 | 12.86 |
| 8.17 | 10.82 |
| 8.93 | 9.89 |
| 14.51 | 6.10 |
| 14.94 | 5.92 |
| 16.84 | 5.26 |
| 19.10 | 4.64 |
| 24.51 | 3.63 |
| 27.28 | 3.27 |

Production Example 9: Production of Cocrystals of Compound (A) and Salicylic Acid To compound (A) (620 mg) in an eggplant flask (100 mL) was added a saturated acetonitrile solution (30 mL) of salicylic acid, the eggplant flask was sealed with a glass stopper under air atmosphere, and the suspension was stirred with a magnetic stirrer at about 450 rpm at room temperature for 5 days. The crystals in the suspension were collected by filtration, washed twice with acetonitrile, and dried under vacuum to give the object cocrystals (735 mg, yield 85.2%) as a white powder. The melting point of the cocrystals measured under the above-mentioned conditions was 176° C. The 2θ and d values of the powder X-ray diffraction peaks of the cocrystals measured under the above-mentioned conditions are shown in Table 10.

TABLE 10 powder X-ray diffraction peaks of cocrystals of compound (A) and salicylic acid

| 2θ (°) | d value (Å) |
|---|---|
| 6.720 | 13.1426 |
| 7.880 | 11.2103 |
| 8.640 | 10.2259 |
| 13.520 | 6.5438 |
| 14.660 | 6.0374 |
| 16.600 | 5.3360 |
| 19.360 | 4.5810 |

TABLE 10-continued powder X-ray diffraction peaks of cocrystals
of compound (A) and salicylic acid

| 2θ (°) | d value (Å) |
|---|---|
| 19.860 | 4.4668 |
| 24.620 | 3.6129 |
| 27.200 | 3.2758 |

The content of salicylic acid in the cocrystal as measured by UPLC under the following conditions was 1.035 mol per 1 mol of compound (A).
system: Aquity UPLC H-Class (Waters)
detector; 214 nm
separation column: YMC Triart-C18 1.9 μm, 2.0×75 mm (YMC Co., Ltd.)
column temperature: 40° C.
mobile phase A: 20 mmol/L sodium hydrogen carbonate buffer (pH 2.5)
mobile phase B: acetonitrile
flow: 0.4 mL/min
analysis time: 20.0 min
injection volume: 2.5 μL
solvent: water/acetonitrile (1:1)

TABLE 11

| gradient | |
|---|---|
| time (min) | concentration (%) of mobile phase B |
| 0 | 1 |
| 1.5 | 1 |
| 6.5 | 75 |
| 10 | 75 |
| 10.01 | 1 |
| 20 | 1 |

Production Example 10: Production of Cocrystals of Compound (A) and Maleic Acid

To compound (A) (680 mg) in an eggplant flask (100 mL) was added a saturated acetonitrile solution (35 mL) of maleic acid, the eggplant flask was sealed with a glass stopper under air atmosphere, and the suspension was stirred with a magnetic stirrer at about 450 rpm at room temperature for 2 hr, a saturated acetonitrile solution (7 mL) of salicylic acid was further add, and the mixture was stirred with a magnetic stirrer at about 700 rpm at room temperature for 5 days. The crystals in the suspension were collected by filtration, washed twice with acetonitrile, and suction dried to give the object cocrystals (753 mg, yield 83.0%) as a white powder. The melting point of the cocrystals measured under the above-mentioned conditions was 188° C. The 2θ and d values of the powder X-ray diffraction peaks of the cocrystals measured under the above-mentioned conditions are shown in Table 12.

TABLE 12 powder X-ray diffraction peaks of cocrystals
of compound (A) and maleic acid

| 2θ (°) | d value (Å) |
|---|---|
| 6.100 | 14.4770 |
| 12.120 | 7.2964 |
| 16.780 | 5.2791 |

TABLE 12-continued powder X-ray diffraction peaks of cocrystals
of compound (A) and maleic acid

| 2θ (°) | d value (Å) |
|---|---|
| 18.380 | 4.8230 |
| 19.520 | 4.5439 |
| 20.660 | 4.2956 |
| 22.060 | 4.0261 |

The content of maleic acid in the cocrystal as measured by ion chromatography under the following conditions was 1.076 mol per 1 mol of compound (A).
system: ICS-1000 (Thermo Fisher Scientific K.K.)
suppressor: ASRS (recycle mode/current value 22 mA)
detector: electric conductivity detector
separation column: IonPac AS12A (4×200 mm, Thermo Fisher Scientific K.K.)
guard column: IonPac AG12A (4×50 mm, Thermo Fisher Scientific K.K.)
column temperature: 30° C.
mobile phase: 2.7 mmol/L aqueous sodium carbonate solution/0.3 mmol/L aqueous sodium hydrogen carbonate solution
flow: 1.5 mL/min
injection volume: 25 μL
solvent: water/DMSO (1:1)

Production Example 11: Production of Cocrystals of Compound (A) and Citric Acid

Compound (A) (20 mg) in a glass tube was dissolved in trifluoroethanol (2.5 mL), and the solvent was removed with nitrogen. After solvent removal, a saturated acetonitrile solution (5 mL) of citric acid was added, and the glass tube was sealed with a plastic stopper under air atmosphere, and the suspension was stirred with a magnetic stirrer at about 450 rpm at room temperature for 7 days. The crystals in the suspension were collected by filtration to give the object cocrystals as a white powder. The melting point of the cocrystals measured under the above-mentioned conditions was 159° C. The 2θ and d values of the powder X-ray diffraction peaks of the cocrystals measured under the above-mentioned conditions are shown in Table 13.

TABLE 13 powder X-ray diffraction peaks of cocrystals
of compound (A) and citric acid

| 2θ (°) | d value (Å) |
|---|---|
| 5.260 | 16.7868 |
| 8.940 | 9.8834 |
| 15.880 | 5.5763 |
| 16.400 | 5.4006 |
| 18.660 | 4.7513 |
| 22.780 | 3.9004 |
| 23.520 | 3.7794 |
| 26.000 | 3.4242 |
| 28.160 | 3.1663 |

The content of citric acid in the cocrystal as measured by ion chromatography under the following conditions was 0.976 mol per 1 mol of compound (A).
system: ICS-1000 (Thermo Fisher Scientific K.K.)
suppressor: ASRS (recycle mode/current value 22 mA)
detector: electric conductivity detector
separation column: IonPac AS14A (4×200 mm, Thermo Fisher Scientific K.K.)
guard column: IonPac AG14A (4×50 mm, Thermo Fisher Scientific K.K.)
column temperature: 30° C.
mobile phase: 8 mmol/L aqueous sodium carbonate solution/1 mmol/L aqueous sodium hydrogen carbonate solution
flow: 0.8 mL/min
injection volume: 25 μL
solvent: water/DMSO (1:1)

Production Example 12: Production of Cocrystals of Compound (A) and Malonic Acid Compound (A) (20 mg) in a glass tube was dissolved in trifluoroethanol (2.5 mL), and the solvent was removed with nitrogen. After solvent removal, a saturated acetonitrile solution (5 mL) of malonic acid was added, and the glass tube was sealed with a plastic stopper under air atmosphere, and the suspension was stirred with a magnetic stirrer at 450 rpm at room temperature for 7 days. The crystals in the suspension were collected by filtration to give the object cocrystals as a white powder. The melting point of the cocrystals measured under the above-mentioned conditions was 165° C. The 2θ and d values of the powder X-ray diffraction peaks of the cocrystals measured under the above-mentioned conditions are shown in Table 14.

TABLE 14

| powder X-ray diffraction peaks of cocrystals of compound (A) and malonic acid | |
|---|---|
| 2θ (°) | d value (Å) |
| 6.340 | 13.9295 |
| 16.760 | 5.2854 |
| 17.520 | 5.0578 |
| 18.740 | 4.7312 |
| 23.800 | 3.7355 |
| 25.140 | 3.5394 |
| 25.780 | 3.4529 |

The content of malonic acid in the cocrystal as measured by ion chromatography under the following conditions was 1.521 mol per 1 mol of compound (A).
system: ICS-1000 (Thermo Fisher Scientific K.K.)
suppressor: ASRS (recycle mode/current value 22 mA)
detector: electric conductivity detector
separation column: IonPac AS12A (4×200 mm, Thermo Fisher Scientific K.K.)
guard column: IonPac AG12A (4×50 mm, Thermo Fisher Scientific K.K.)
column temperature: 30° C.
mobile phase: 2.7 mmol/L aqueous sodium carbonate solution/0.3 mmol/L aqueous sodium hydrogen carbonate solution
flow: 1.5 mL/min
injection volume: 25 μL
solvent: DMSO/water (1:1)

Production Example 13: Production of Cocrystals of Compound (A) and Malic Acid

Compound (A) (20 mg) in a glass tube was dissolved in trifluoroethanol (2.5 mL), and the solvent was removed with nitrogen. After solvent removal, a saturated acetonitrile solution (5 mL) of L-malic acid was added, and the glass tube was sealed with a plastic stopper under air atmosphere, and the suspension was stirred with a magnetic stirrer at about 450 rpm at room temperature for 7 days. The crystals in the suspension were collected by filtration to give the object cocrystals as a white powder. The melting point of the cocrystals measured under the above-mentioned conditions was 161° C. The 2θ and d values of the powder X-ray diffraction peaks of the cocrystals measured under the above-mentioned conditions are shown in Table 15.

TABLE 15

| powder X-ray diffraction peaks of cocrystals of compound (A) and malic acid | |
|---|---|
| 2θ (°) | d value (Å) |
| 5.800 | 15.2251 |
| 6.540 | 13.5039 |
| 16.680 | 5.3106 |
| 16.820 | 5.2667 |
| 16.980 | 5.2174 |
| 20.340 | 4.3625 |
| 26.420 | 3.3707 |
| 26.620 | 3.3459 |

The content of malic acid in the cocrystal as measured by ion chromatography under the following conditions was 0.993 mol per 1 mol of compound (A).
system: ICS-1000 (Thermo Fisher Scientific K.K.)
suppressor: ASRS (recycle mode/current value 22 mA)
detector: electric conductivity detector
separation column: IonPac AS12A (4×200 mm, Thermo Fisher Scientific K.K.)
guard column: IonPac AG12A (4×50 mm, Thermo Fisher Scientific K.K.)
column temperature: 30° C.
mobile phase: 2.7 mmol/L aqueous sodium carbonate solution/0.3 mmol/L aqueous sodium hydrogen carbonate solution
flow: 1.5 mL/min
injection volume: 25 μL
solvent: DMSO/water (1:1)

Production Example 14: Production of Cocrystals of Compound (A) and Mandelic Acid Compound (A) (20 mg) in a glass tube was dissolved in trifluoroethanol (2.5 mL), and the solvent was removed with nitrogen. After solvent removal, a saturated acetonitrile solution (5 mL) of (+/−)-mandelic acid was added, and the glass tube was sealed with a plastic stopper under air atmosphere, and the suspension was stirred with a magnetic stirrer at about 450 rpm at room temperature for 7 days. The crystals in the suspension were collected by filtration to give the object cocrystals as a white powder. The melting points of the cocrystals measured under the above-mentioned conditions were 107° C. and 136° C. The 2θ and d values of the powder X-ray diffraction peaks of the cocrystals measured under the above-mentioned conditions are shown in Table 16.

TABLE 16 powder X-ray diffraction peaks of cocrystals
of compound (A) and mandelic acid

| 2θ (°) | d value (Å) |
|---|---|
| 5.380 | 16.4127 |
| 10.900 | 8.1102 |
| 12.980 | 6.8148 |
| 16.840 | 5.2605 |
| 20.080 | 4.4184 |
| 21.960 | 4.0442 |
| 25.420 | 3.5010 |
| 26.300 | 3.3858 |
| 28.000 | 3.1840 |

The content of mandelic acid in the cocrystal as measured by ion chromatography under the following conditions was 1.531 mol per 1 mol of compound (A).
- system: ICS-1000 (Thermo Fisher Scientific K.K.)
- suppressor: ASRS (recycle mode/current value 22 mA)
- detector: electric conductivity detector
- separation column: IonPac AS12A (4×200 mm, Thermo Fisher Scientific K.K.)
- guard column: IonPac AG12A (4×50 mm, Thermo Fisher Scientific K.K.)
- column temperature: 30° C.
- mobile phase: 2.7 mmol/L aqueous sodium carbonate solution/0.3 mmol/L aqueous sodium hydrogen carbonate solution
- flow: 1.5 mL/min
- injection volume: 25 μL
- solvent: DMSO/water (1:1)

Production Example 15: Production of Cocrystals of Compound (A) and Gentisic Acid Distilled water (about 10 mL) was added to gentisic acid (about 1 g), and the mixture was suspended and stirred with a magnetic stirrer at room temperature for 24 hr. Undissolved gentisic acid was removed by filtration to prepare a saturated aqueous solution of gentisic acid. To the saturated aqueous solution (10 mL) was added compound (A) (about 50 mg), and the mixture was stirred with a magnetic stirrer and the obtained suspension was stirred at room temperature for one day. The crystals were collected by filtration and the obtained wet crystals were air-dried to give the object cocrystals.

Figure 4:
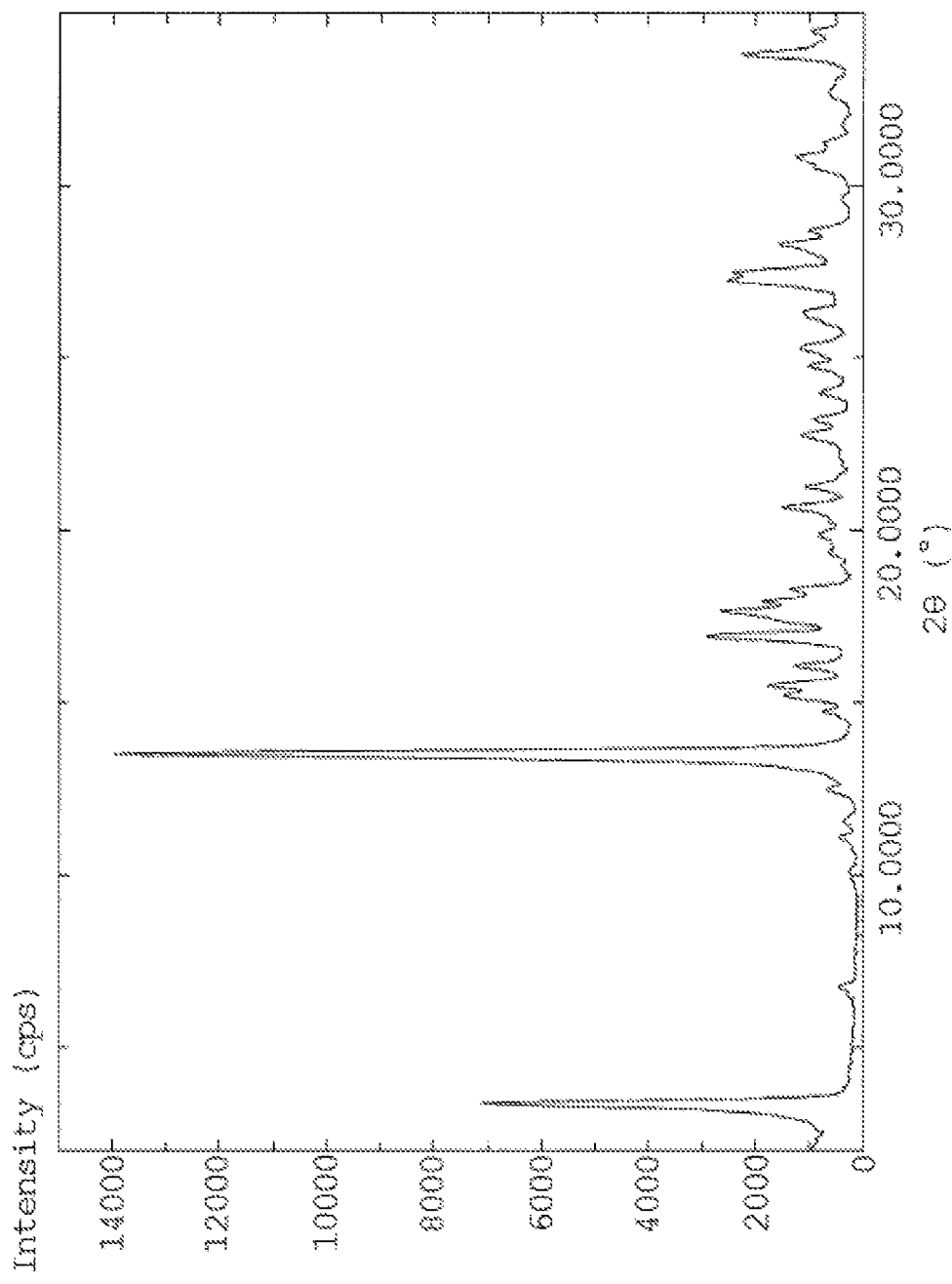
FIG. 4 is a powder X-ray diffraction chart of the cocrystals of compound (A) and gentisic acid, which were obtained in Production Example 15.

The water content of the obtained cocrystals by Karl Fischer moisture measurement (measuring apparatus: "AQ-7" manufactured by HIRANUMA SANGYO Co., Ltd., solution: Aqualyte RS-A, room temperature: about 26° C., relative humidity: about 33%) was 6.2%. From this water content, it was confirmed that the obtained cocrystal was a trihydrate. In TGA and DSC of the obtained cocrystals, a weight loss of about 2.2% or more was observed between 25° C. and about 80° C., followed by a weight loss of about 1.8% between about 80° C. and about 140° C., along with which the cocrystals melted. Powder X-ray diffraction of the obtained cocrystals was measured under the above-mentioned conditions to find a powder X-ray diffraction pattern having characteristic peaks at lattice spacings (d) of about 25.97, 13.06, 7.98, 7.64, 7.08, 6.54, 6.01, 5.24 and 5.02 angstroms. The 2θ and d values of the powder X-ray diffraction peaks of the cocrystals measured under the above-mentioned conditions are shown in Table 17. The powder X-ray diffraction chart of the cocrystals obtained by measurement under the above-mentioned conditions is shown in FIG. 4.

TABLE 17 powder X-ray diffraction peaks of cocrystals of compound (A)
and gentisic acid

| 2θ (°) | d value (Å) |
|---|---|
| 3.40 | 25.97 |
| 6.76 | 13.06 |
| 11.08 | 7.98 |
| 11.58 | 7.64 |
| 12.50 | 7.08 |
| 13.52 | 6.54 |
| 14.72 | 6.01 |
| 16.92 | 5.24 |
| 17.64 | 5.02 |

The content of gentisic acid in the cocrystal as measured by UPLC under the following conditions was 3.07 mol per 1 mol of compound (A).
- system: Aquity UPLC H-Class (Waters)
- detector: 214 nm
- separation column: YMC Triart-C18 1.9 μm, 2.0×75 mm (YMC Co., Ltd.)
- column temperature: 40° C.
- mobile phase A: 20 mmol/L sodium hydrogen carbonate buffer (pH 2.5)
- mobile phase B: acetonitrile
- flow: 0.4 mL/min
- analysis time: 20.0 min
- injection volume: 2.5 μL
- solvent: water/acetonitrile (1:1)

TABLE 18

| gradient | |
|---|---|
| time (min) | concentration (%) of mobile phase B |
| 0 | 1 |
| 1.5 | 1 |
| 6.5 | 75 |
| 10 | 75 |
| 10.01 | 1 |
| 20 | 1 |

Production Example 16: Production of Cocrystals of Compound (A) and Gentisic Acid Distilled water (about 10 mL) was added to gentisic acid (about 1 g), and the mixture was suspended and stirred with a magnetic stirrer at room temperature for 24 hr. Then, undissolved gentisic acid was removed by filtration to prepare a saturated aqueous solution of gentisic acid. To the saturated aqueous solution (10 mL) was added compound (A) (about 50 mg), and the mixture was stirred with a magnetic stirrer and the obtained suspension was stirred at room temperature for one day. The crystals were collected by filtration and the obtained wet crystals were air-dried and dried under reduced pressure at about 25° C. for 3 hr to give the object cocrystals.

Figure 5:
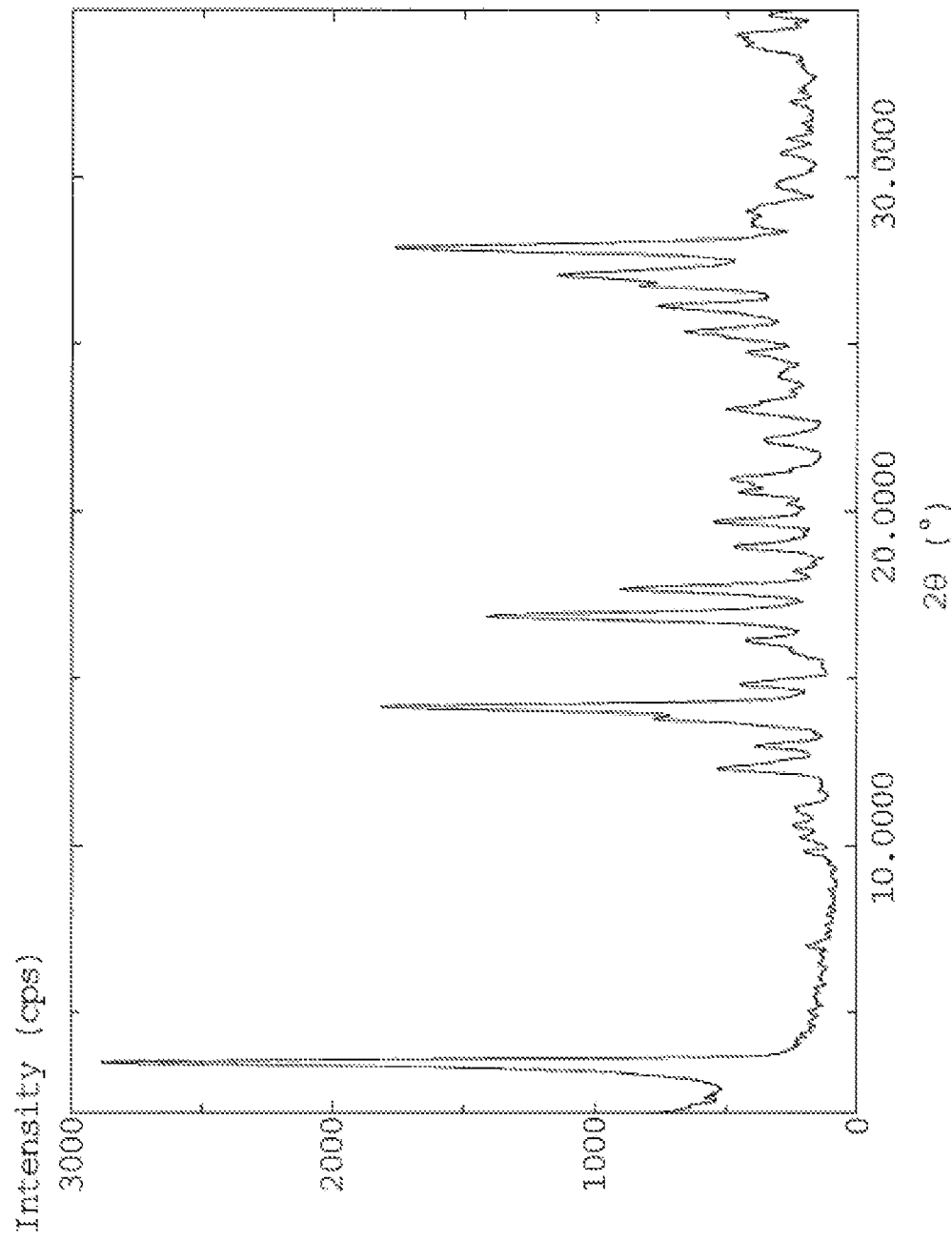
FIG. 5 is a powder X-ray diffraction chart of the cocrystals of compound (A) and gentisic acid, which were obtained in Production Example 16.

The water content of the obtained cocrystals by Karl Fischer moisture measurement under the same conditions as in Production Example 15 was 2.5%. From this water content, it was confirmed that the obtained cocrystal was a monohydrate. In TGA and DSC of the obtained cocrystals, a weight loss of about 2.4% was observed between about 80° C. and about 140° C., along with which the cocrystals melted. Powder X-ray diffraction of the obtained cocrystals was measured under the above-mentioned conditions to find a powder X-ray diffraction pattern having characteristic peaks at lattice spacings (d) of about 25.08, 9.02, 7.20, 6.83, 6.42, 6.25, 5.98, 5.25 and 5.01 angstroms. The 2θ and d values of the powder X-ray diffraction peaks of the cocrystals measured under the above-mentioned conditions are shown in Table 19. The powder X-ray diffraction chart of the cocrystals obtained by measurement under the above-mentioned conditions is shown in FIG. 5.

TABLE 19 powder X-ray diffraction peaks of cocrystals of compound (A) and gentisic acid

| 2θ (°) | d value (Å) |
|---|---|
| 3.52 | 25.08 |
| 9.80 | 9.02 |
| 12.28 | 7.20 |
| 12.96 | 6.83 |
| 13.78 | 6.42 |
| 14.16 | 6.25 |
| 14.80 | 5.98 |
| 16.86 | 5.25 |
| 17.68 | 5.01 |

The content of gentisic acid in the cocrystal as measured by UPLC under the following conditions was 3.05 mol per 1 mol of compound (A).

system: Aquity UPLC H-Class (Waters)
detector: 214 nm
separation column: YMC Triart-C18 1.9 μm, 2.0×75 mm (YMC Co., Ltd.)
column temperature: 40° C.
mobile phase A: 20 mmol/L sodium hydrogen carbonate buffer (pH 2.5)
mobile phase B: acetonitrile
flow: 0.4 mL/min
analysis time: 20.0 min
injection volume: 2.5 μL
solvent: water/acetonitrile (1:1)

TABLE 20

| gradient | |
|---|---|
| time (min) | concentration (%) of mobile phase B |
| 0 | 1 |
| 1.5 | 1 |
| 6.5 | 75 |
| 10 | 75 |
| 10.01 | 1 |
| 20 | 1 |

Experimental Example 1: Measurement of Solubility

According to the method described in "Thermodynamic Solubility Measurement by the Shake-Flask Method" on page 1229 of Nakashima S., Chem. Pharm. Bull., 61(12) 1228-1238 (2013), the solubility of the crystals and cocrystals of compound (A) was measured. To be specific, the first fluid (JP1), the second fluid (JP2) and the second fluid containing 20 mM sodium glycochenodeoxycholate (JP2/GCDC) of the Japanese Pharmacopoeia disintegration test were added at 400 μL each to the crystals or cocrystals (0.4 mg) of compound (A), and the mixture was heated to 37° C. under air atmosphere, and shaken by a vortex mixer for 2 hr at 500 rpm. After shaking, the mixture was passed through a 0.45 μm PVDF filter, and the filtrate was analyzed by HPLC. From a chromatogram comparison with the standard solution (0.1 mg/mL), the solubility of the crystals of the single compound and the cocrystals was calculated. The results are shown in Table 21.

TABLE 21

| | organic acid in cocrystal | solubility (μg/mL) | | |
|---|---|---|---|---|
| | | JP1 | JP2 | JP2/GCDC |
| crystal of compound (A) | — | 1.5 | 1.5 | 35.6 |
| cocrystal of Production Example 1 | gentisic acid | 14 | 3.6 | 302.3 |
| cocrystal of Production Example 9 | salicylic acid | 8.7 | 8.5 | 302.2 |
| cocrystal of Production Example 10 | maleic acid | 6.1 | 7.5 | 253.5 |
| cocrystal of Production Example 11 | citric acid | 1.9 | 2 | 357.7 |
| cocrystal of Production Example 12 | malonic acid | 4.8 | 12 | 611.6 |
| cocrystal of Production Example 13 | malic acid | 3.1 | 3.7 | 452.4 |
| cocrystal of Production Example 14 | mandelic acid | 2.2 | 3.8 | 422 |
| cocrystal of Production Example 15 | gentisic acid | 2.4 | 2.9 | 71 |
| cocrystal of Production Example 16 | gentisic acid | 2.1 | 2.5 | 110 |

Experimental Example 2: Measurement of Dissolution Rate

According to the method described in "2.6. Intrinsic dissolution test" on page 231 of Tsutsumi S., Int. J. Pharm., 421 (2011) 230-236, the dissolution rate of the crystals and cocrystals of compound (A) was measured. To be specific, the crystals or cocrystals of compound (A) (20 mg) was pressurized by a hand press tableting machine at 20 MPa for 10 min to give a 7 mm diameter disc. The prepared disc was adhered to the inside of a rotating shaft of the United States Pharmacopeia dissolution test 1 (basket), and inserted, while rotating at 200 rpm, in the second fluid (250 mL) of the Japanese Pharmacopoeia disintegration test containing cholic acid heated to 37° C. The second fluid containing the crystals or cocrystals was collected by 0.5 mL at 1 min intervals, and analyzed by HPLC. From a chromatogram comparison with the standard solution (0.05 mg/mL), the concentration of the crystals or the cocrystals was calculated, and the dissolution rate thereof was calculated. The results of the dissolution rate are shown in Table 22.

TABLE 22

| | organic acid in cocrystal | dissolution rate (μg/mm$^2$/min) |
|---|---|---|
| crystal of compound (A) | — | 0.2 |
| cocrystal of Production Example 1 | gentisic acid | 7.7 |
| cocrystal of Production Example 9 | salicylic acid | 8.2 |
| cocrystal of Production Example 10 | maleic acid | 7 |
| cocrystal of Production Example 11 | citric acid | 2.3 |
| cocrystal of Production Example 12 | malonic acid | 3.0 |
| cocrystal of Production Example 13 | malic acid | 1.4 |
| cocrystal of Production Example 14 | mandelic acid | 1.2 |

Production Example 17: Production of Formulation 1 Containing Cocrystals of Compound (A)

The cocrystals obtained in Production Example 8 (pulverized product, 86.4 mg), D-mannitol (1917.6 mg, PEARLITOL 100SD, manufactured by ROQUETTE), microcrystalline cellulose (240 mg, CEOLUS PH-102, manufactured by Asahi Kasei Corporation), croscarmellose sodium (120 mg, Ac-Di-Sol, manufactured by FMC Corporation), and light anhydrous silicic acid (12 mg, AEROSIL 200 Pharma, manufactured by NIPPON AEROSIL CO., LTD.) were weighed in a mortar, and mixed with a pestle. Magnesium stearate (24 mg, manufactured by TAIHEI CHEMICAL INDUSTRIAL CO., LTD.) was added and mixed therewith to give a mixed powder. Using a desk-top tablet press (HANDTAB-200, manufactured by ICHIHASHI SEIKI CO., LTD.), and the mixed powder was compressed at compression force 10 kN to give formulation 1 (tablet) (diameter 8 mm, 200 mg per one tablet). The composition per one tablet of formulation 1 is shown in Table 23.

TABLE 23

| composition per one tablet of formulation 1 | |
| --- | --- |
| component | amount (mg) |
| cocrystal of Production Example 8 (pulverized product) (as compound (A)) | 7.2 (5) |
| D-mannitol (PEARITOL 100SD) | 159.8 |
| microcrystalline cellulose (CEOLUS PH-102) | 20 |
| croscarmellose sodium (Ac-Di-Sol) | 10 |
| light anhydrous silicic acid (AEROSIL 200 Pharma) | 1 |
| magnesium stearate | 2 |
| total | 200 |

Production Example 18: Production of Formulation 2 Containing Cocrystals of Compound (A)

The cocrystals obtained in Production Example 8 (pulverized product, 86.4 mg), D-mannitol (1845.6 mg, PEARLITOL 100SD, manufactured by ROQUETTE), microcrystalline cellulose (240 mg, CEOLUS PH-102, manufactured by Asahi Kasei Corporation), hydroxypropylcellulose (72 mg, grade L, manufactured by Nippon Soda Co., Ltd.), croscarmellose sodium (120 mg, Ac-Di-Sol, manufactured by FMC Corporation), and light anhydrous silicic acid (12 mg, AEROSIL 200 Pharma, manufactured by NIPPON AEROSIL CO., LTD.) were weighed in a mortar, and mixed with a pestle. Magnesium stearate (24 mg, manufactured by TAIHEI CHEMICAL INDUSTRIAL CO., LTD.) was added and mixed therewith to give a mixed powder. Using a desk-top tablet press (HANDTAB-200, manufactured by ICHIHASHI SEIKI CO., LTD.), and the mixed powder was compressed at compression force 10 kN to give formulation 2 (tablet) (diameter 8 mm, 200 mg per one tablet). The composition per one tablet of formulation 2 is shown in Table 24.

TABLE 24

| composition per one tablet of formulation 2 | |
| --- | --- |
| component | amount (mg) |
| cocrystal of Production Example 8 (pulverized product) (as compound (A)) | 7.2 (5) |
| D-mannitol (PEARITOL 100SD) | 153.8 |
| microcrystalline cellulose (CEOLUS PH-102) | 20 |
| hydroxypropylcellulose (HPC-L) | 6 |
| croscarmellose sodium (Ac-Di-Sol) | 10 |
| light anhydrous silicic acid (AEROSIL 200 Pharma) | 1 |
| magnesium stearate | 2 |
| total | 200 |

Production Example 19: Production of Formulation 3 Containing Cocrystals of Compound (A)

The cocrystals obtained in Production Example 8 (pulverized product, 86.4 mg), D-mannitol (1821.6 mg, PEARLITOL 200SD, manufactured by ROQUETTE), microcrystalline cellulose (240 mg, CEOLUS PH-102, manufactured by Asahi Kasei Corporation), hydroxypropylcellulose (72 mg, grade L, manufactured by Nippon Soda Co., Ltd.), croscarmellose sodium (120 mg, Ac-Di-Sol, manufactured by FMC Corporation), and light anhydrous silicic acid (12 mg, AEROSIL 200 Pharma, manufactured by NIPPON AEROSIL CO., LTD.) were weighed in a mortar, and mixed with a pestle. Magnesium stearate (48 mg, manufactured by TAIHEI CHEMICAL INDUSTRIAL CO., LTD.) was added and mixed therewith to give a mixed powder. Using a desk-top tablet press (HANDTAB-200, manufactured by ICHIHASHI SEIKI CO., LTD.), and the mixed powder was compressed at compression force 9 kN to give formulation 3 (tablet) (diameter 8 mm, 200 mg per one tablet). The composition per one tablet of formulation 3 is shown in Table 25.

TABLE 25

| composition per one tablet of formulation 3 | |
| --- | --- |
| component | amount (mg) |
| cocrystal of Production Example 8 (pulverized product) (as compound (A)) | 7.2 (5) |
| D-mannitol (PEARITOL 200SD) | 151.8 |
| microcrystalline cellulose (CEOLUS PH-102) | 20 |
| hydroxypropylcellulose (HPC-L) | 6 |
| croscarmellose sodium (Ac-Di-Sol) | 10 |
| light anhydrous silicic acid (AEROSIL 200 Pharma) | 1 |
| magnesium stearate | 4 |
| total | 200 |

Production Example 20: Production of Formulation 4 Containing Cocrystals of Compound (A)

The cocrystals obtained in Production Example 8 (pulverized product, 86.4 mg), D-mannitol (1581.6 mg, PEARLITOL 200SD, manufactured by ROQUETTE), microcrystalline cellulose (480 mg, CEOLUS PH-102, manufactured by Asahi Kasei Corporation), hydroxypropylcellulose (72 mg, grade L, manufactured by Nippon Soda Co., Ltd.), croscarmellose sodium (120 mg, Ac-Di-Sol, manufactured by FMC Corporation), and light anhydrous silicic acid (12 mg, AEROSIL 200 Pharma, manufactured by NIPPON AEROSIL CO., LTD.) were weighed in a mortar, and mixed with a pestle. Magnesium stearate (48 mg, manufactured by TAIHEI CHEMICAL INDUSTRIAL CO., LTD.) was added and mixed therewith to give a mixed powder. Using a desk-top tablet press (HANDTAB-200, manufactured by ICHIHASHI SEIKI CO., LTD.), and the mixed powder was compressed at a compression force 9 kN to give formulation 4 (tablet) (diameter 8 mm, 200 mg per one tablet). The composition per one tablet of formulation 4 is shown in Table 26.

TABLE 26 composition per one tablet of formulation 4

| component | amount (mg) |
| --- | --- |
| cocrystal of Production Example 8 | 7.2 |
| (pulverized product) | (5) |
| (as compound (A)) | |
| D-mannitol (PEARITOL 200SD) | 131.8 |
| microcrystalline cellulose (CEOLUS PH-102) | 40 |
| hydroxypropylcellulose (HPC-L) | 6 |
| croscarmellose sodium (Ac-Di-Sol) | 10 |
| light anhydrous silicic acid (AEROSIL 200 Pharma) | 1 |
| magnesium stearate | 4 |
| total | 200 |

Production Example 21: Production of Formulation 5 Containing Cocrystals of Compound (A)

The cocrystals (71.96 g) obtained in Production Example 4, D-mannitol (312.04 g, PEARLITOL 200SD, manufactured by ROQUETTE), microcrystalline cellulose (60 g, CEOLUS UF-702, manufactured by Asahi Kasei Corporation), hydroxypropylcellulose (24 g, grade L, manufactured by Nippon Soda Co., Ltd.), low substituted hydroxypropylcellulose (60 g, grade LH-B1, manufactured by Shin-Etsu Chemical Co., Ltd.), and light anhydrous silicic acid (3 g, AEROSIL 200 Pharma, manufactured by NIPPON AEROSIL CO., LTD.) were weighed and mixed to give a primary mixed powder. The primary mixed powder was weighed by 398.3 g, microcrystalline cellulose (45 g, CEOLUS KG-802, manufactured by Asahi Kasei Corporation) and magnesium stearate (6.75 g, manufactured by TAIHEI CHEMICAL INDUSTRIAL CO., LTD.) were added, and they were mixed to give a secondary mixed powder. The obtained secondary mixed powder was compressed by a rotary tablet press (Correct 19K, manufactured by KIKUSUI SEISAKUSHO LTD.) at compression force 6 kN to give an uncoated tablet (diameter 9 mm, 300 mg per one tablet). An aqueous dispersion of OPADRY (manufactured by Colorcon Japan LLC) was sprayed on the uncoated tablets (150 g) in DRIACOATER (DRC-200, manufactured by Powrex Corporation) such that the film coating amount per one tablet was 12 mg to give formulation 5 (tablet). The composition per one tablet of formulation 5 is shown in Table 27.

TABLE 27 composition per one tablet of formulation 5

| component | amount (mg) |
| --- | --- |
| cocrystal of Production Example 4 | 35.98 |
| (as compound (A)) | (25) |
| D-mannitol (PEARITOL 200SD) | 156.02 |
| microcrystalline cellulose (CEOLUS UF-702) | 30 |
| hydroxypropylcellulose (HPC-L) | 12 |
| low substituted hydroxypropylcellulose (LH-B1) | 30 |
| light anhydrous silicic acid (AEROSIL 200 Pharma) | 1.5 |
| microcrystalline cellulose (CEOLUS KG-802) | 30 |
| magnesium stearate | 4.5 |
| OPADRY | 12 |
| total | 312 |

Production Example 22: Production of Formulation 6 Containing Cocrystals of Compound (A)

The cocrystals (79.16 g) obtained in Production Example 4, D-mannitol (154.48 g, PEARLITOL 50C, manufactured by ROQUETTE), microcrystalline cellulose (33 g, CEOLUS PH-101, manufactured by Asahi Kasei Corporation), and low substituted hydroxypropylcellulose (24.75 g, grade LH-B1, manufactured by Shin-Etsu Chemical Co., Ltd.) were weighed and placed in a fluid bed granulator (LAB-1, manufactured by Powrex Corporation), granulated by spraying an aqueous solution of 6(w/w) % hydroxypropylcellulose (grade L, manufactured by Nippon Soda Co., Ltd.) (165 g), and dried to give granules. The granules were sieved, and the obtained sieved granules (219.1 g) were weighed. Low substituted hydroxypropylcellulose (18 g, grade LH-B1, manufactured by Shin-Etsu Chemical Co., Ltd.) and magnesium stearate (2.88 g, manufactured by TAIHEI CHEMICAL INDUSTRIAL CO., LTD.) were added and mixed to give a mixed granules. The obtained mixed granules were compressed by a rotary tablet press (Correct 19K, manufactured by KIKUSUI SEISAKUSHO LTD.) at compression force 6 kN to give an uncoated tablet (diameter 7 mm, 150 mg per one tablet). An aqueous dispersion of OPADRY (manufactured by Colorcon Japan LLC) was sprayed on the uncoated tablets (150 g) in DRIACOATER (DRC-200, manufactured by Powrex Corporation) such that the film coating m amount per one tablet was 6 mg to give formulation 6 (tablet). The composition per one tablet of formulation 6 is shown in Table 28.

TABLE 28 composition per one tablet of formulation 6

| component | amount (mg) |
| --- | --- |
| cocrystal of Production Example 4 | 35.98 |
| (as compound (A)) | (25) |
| D-mannitol (PEARITOL 50C) | 70.22 |
| microcrystalline cellulose (CEOLUS PH-101) | 15 |
| low substituted hydroxypropylcellulose (LH-B1) | 22.5 |
| hydroxypropylcellulose (HPC-L) | 4.5 |
| magnesium stearate | 1.8 |
| OPADRY | 6 |
| total | 156 |

Experimental Example 3: Measurement of Thickness, Hardness and Disintegration Time of Formulation The thickness, hardness and disintegration time of the formulations 1-4 obtained in Production Examples 17-20 were measured. The disintegration test was performed according to the Japanese Pharmacopoeia disintegration test method (test solution: water, 37° C., no disc). The results are shown in Table 29.

TABLE 29

|  | formulation 1 | formulation 2 | formulation 3 | formulation 4 |
|---|---|---|---|---|
| thickness (mm) | 4.15 | 4.17 | 4.19 | 4.14 |
| hardness (N) | 165.1 | 149.5 | 98.6 | 109.0 |
| disintegration time (sec) | 35 | 44 | 74 | 87 |

Experimental Example 4: Pharmacokinetic Test 1

Using the cocrystals obtained in Production Examples 1, 9 and 10, a pharmacokinetic test of compound (A) was performed by oral administration to a beagle dog.

The dose was set to 10 mg as compound (A), the cocrystals (14.4 mg) obtained in Production Example 1, the cocrystals (14.1 mg) obtained in Production Example 9 or the cocrystals (13.6 mg) obtained in Production Example 10 (each 10 mg as compound (A)) were filled in gelatin capsules to give formulations 7-9 (capsule). One capsule each of the obtained formulations 7-9 was orally administered to a beagle dog as described below.

Each of the obtained formulations was orally administered to a beagle dog (male, 5 heads) in a fasted state. Each formulation was administered to the same group of 5 beagle dogs. In each administration, a pre-administration treatment with a pentagastrin solution was performed 15 minutes before the administration. The blood samples were collected 15 and 30 min, and 1, 2, 4, 6, 8, 12 and 24 hr after administration, and centrifuged to give plasma. The plasma concentration of compound (A) was measured using LC and MS/MS under the following conditions.
LC Conditions
Analytical column: Kinetex C18, 50 mm×2.0 mm I.D., 2.6 µm (Phenomenex)
Column oven temperature: 40° C.
Mobile phase: Purified water/acetonitrile/formic acid (600:200:0.1, v/v/v)
Flow rate: 0.2 mL/min
Injection volume: 20 µL
Autosampler temperature: 10° C.
Rinsing solution: Acetonitrile/purified water/formic acid (600:400:0.1, v/v/v)
Running time: 5.0 minutes
The effluent from 2.0 to 5.0 minutes was transferred to the MS/MS by valve operation.
MS/MS Conditions
Ionization mode: Turbo ion spray
Polarity: Positive
Scan type: Selected reaction monitoring
Ionspray voltage: 5500 V
Turbo probe temperature: 600° C.
Interface heater: ON
Curtain gas pressure: 0.28 MPa (40 psi, $N_2$)
Ion source gas 1 pressure: 0.28 MPa (40 psi, Air)
Ion source gas 2 pressure: 0.28 MPa (40 psi, Air)
Collision gas pressure: 8 Bit ($N_2$)
Dwell time: 0.8 seconds (for compound (A)) and 0.2 seconds (for
internal standard (Compound (A)-$d_3$ which is compound (A) wherein 3 hydrogen atoms are deuterated))
Duration time: 5.0 minutes

TABLE 30

| Monitor ion and parameters: | | | | | | |
|---|---|---|---|---|---|---|
| | Precursor ion (m/z) | → | Production (m/z) | DP[*1] (V) | EP[*2] (V) | CE[*3] (V) | CXP[*4] (V) |
| compound (A) | 352.3 | → | 124.1 | 131 | 10 | 23 | 20 |
| internal standard (Compound (A)-$d_3$ [*5]) | 355.0 | → | 127.2 | 106 | 10 | 23 | 18 |

Figure 6:
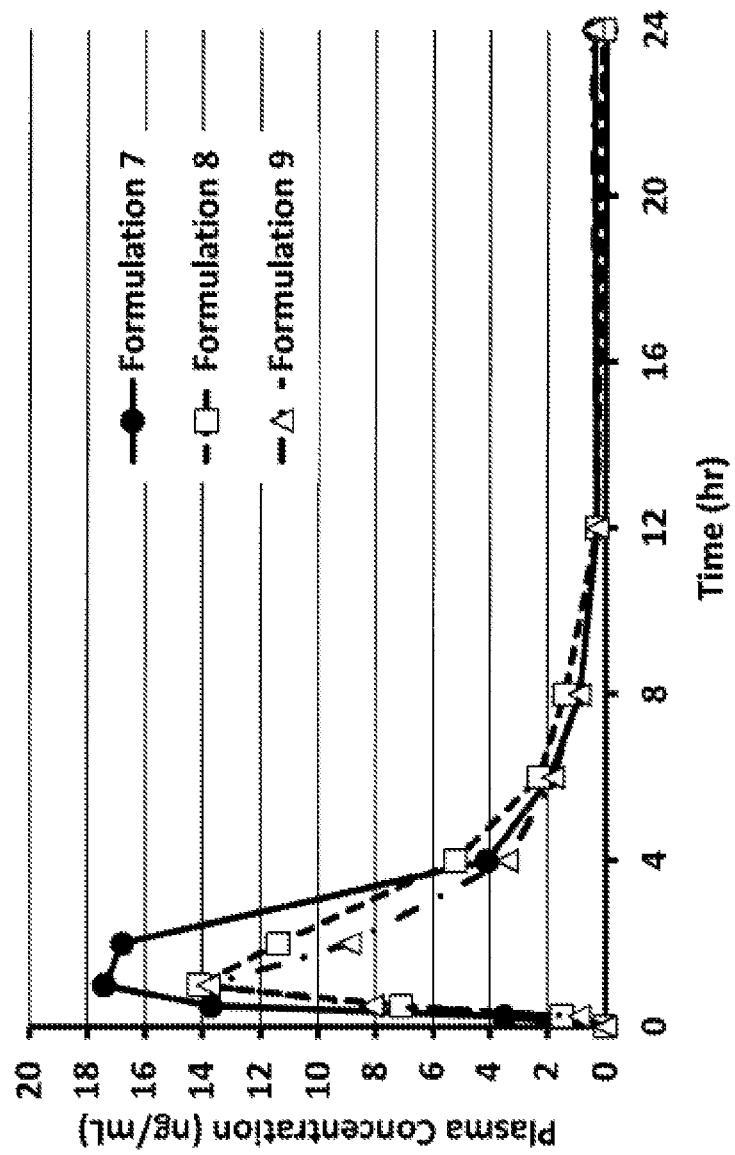
FIG. 6 is a graph showing a curve of a plasma concentration of compound (A) and time, which was obtained by the measurement in Experimental Example 4.

[*1]Declustering Potential
[*2]Entrance Potential
[*3]Collision Energy
[*4]Collision Cell Exit Potential
[*5] Compound (A) wherein 3 hydrogen atoms are deuterated The maximum blood concentration ($C_{max}$) and the maximum blood concentration reaching time ($T_{max}$) of the drug (compound (A)) were calculated from the plasma concentration and time curve of compound (A). In addition, the area under the blood concentration-time curve ($AUC_{0-24h}$) of 0 to 24 hours was calculated by the linear trapidoidal method. The results are shown in Table 31 and FIG. 6. The values such as $T_{max}$ and the like in Table 31 are average values, and the numerical values in parentheses indicate standard deviation (S.D.).

TABLE 31

| formulation | cocrystal in formulation | organic acid in cocrystal | dose [*1] (mg/head) | $T_{max}$ (hr) | $C_{max}$ (ng/mL) | $AUC_{0-24h}$ (ng·h/mL) |
|---|---|---|---|---|---|---|
| formulation 7 | cocrystal of Production Example 1 | gentisic acid | 10 | 1.1 (0.5) | 18.8 (7.7) | 63.8 (22.5) |
| formulation 8 | cocrystal of Production Example 9 | salicylic acid | 10 | 1.4 (0.5) | 14.7 (6.2) | 52.7 (14.7) |
| formulation 9 | cocrystal of Production Example 10 | maleic acid | 10 | 1.5 (0.7) | 14.5 (15.3) | 45.8 (27.7) |

[*1] dose as compound (A)

Experimental Example 5: Pharmacokinetic Test 2

Using the following two kinds of formulations, a pharmacokinetic test of compound (A) was performed by oral administration to a beagle dog.
(1) Formulation 10 (IR Tablet)

Water was added to compound (A), D-mannitol, microcrystalline cellulose, hydroxypropylcellulose and sodium carboxymethyl starch, and the mixture was granulated in a mortar and dried to give granules. Magnesium stearate was added to the granules to give mixed granules. Using a desk-top tablet press (HANDTAB-200, ICHIHASHI SEIKI CO., LTD.), a tablet containing 300 mg of compound (A) per tablet (tablet total: 400 mg, major axis: 12 mm×minor axis: 7 mm) was produced at compression force 10 kN. The dose was set to 300 mg, and one tablet was orally administered to a beagle dog. The composition per one tablet of formulation 10 is shown in Table 32.

TABLE 32 composition per one tablet of formulation 10

| component | amount (mg) |
|---|---|
| compound (A) | 300 |
| D-mannitol | 43 |
| microcrystalline cellulose | 30 |
| hydroxypropylcellulose | 9 |
| sodium carboxymethyl starch | 15 |
| magnesium stearate | 3 |
| total | 400 |

(2) Formulation 11 (Capsule)

The dose was set to 100 mg as compound (A), the cocrystal (144 mg) obtained in Production Example 1 (100 mg as compound (A)) were filled in a gelatin capsule to give formulation 11 (capsule) and one capsule each was orally administered to a beagle dog.

Each of the obtained formulations was orally administered to a beagle dog (male, 5 heads) in a fasted state. Each formulation was administered to the same group of 5 beagle dogs. In each administration, a pre-administration treatment with a pentagastrin solution was performed 15 minutes before the administration. The blood samples were collected 15 and 30 min, and 1, 2, 4, 6, 8, 12 and 24 hr after administration, and centrifuged to give plasma. The plasma concentration of compound (A) was measured using LC and MS/MS under the conditions shown in Experimental Example 4.

Figure 7:
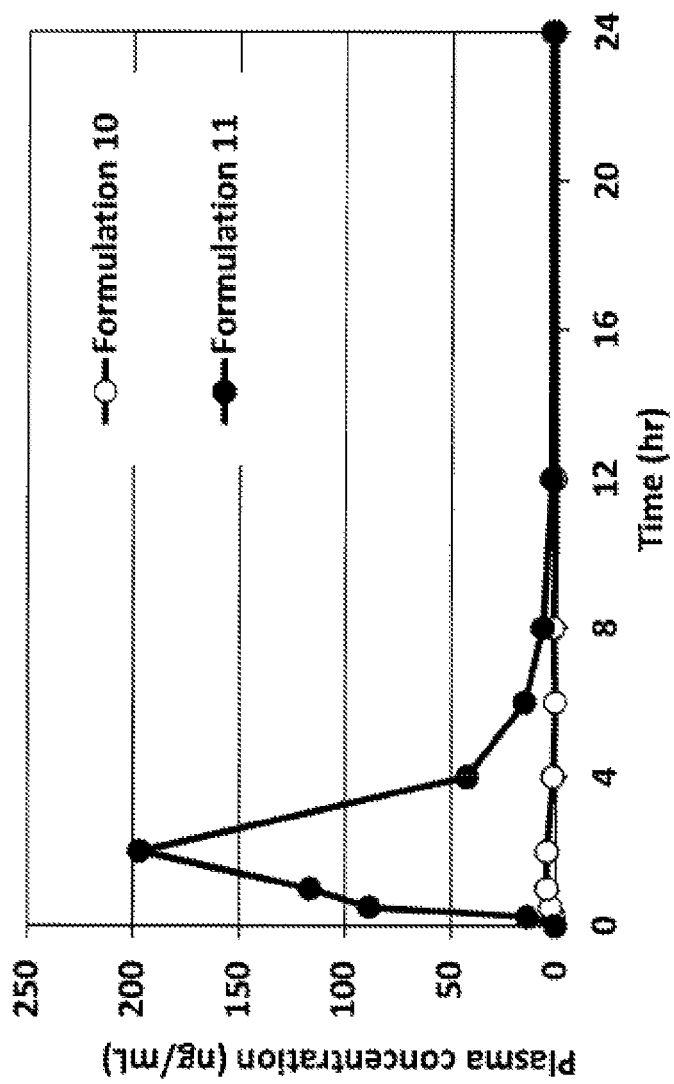
FIG. 7 is a graph showing a curve of a plasma concentration of compound (A) and time, which was obtained by the measurement in Experimental Example 5.

The maximum blood concentration ($C_{max}$) and the maximum blood concentration reaching time ($T_{max}$) of the drug (compound (A)) were calculated from the plasma concentration and time curve of compound (A). In addition, the area under the blood concentration-time curve ($AUC_{0-24h}$) of 0 to 24 hours was calculated by the linear trapidoidal method. The results are shown in Table 33 and FIG. 7. The values such as $T_{max}$ and the like in Table 33 are average values, and the numerical values in parentheses indicate standard deviation (S.D.).

TABLE 33

| formulation | active ingredient in formulation | dose *[1] (mg/head) | $T_{max}$ (hr) | $C_{max}$ (ng/mL) | $AUC_{0-24\ h}$ (ng · h/mL) |
|---|---|---|---|---|---|
| formulation 10 | compound (A) | 300 | 1.6 (0.5) | 4.7 (1.0) | 30.2 (14.5) |
| formulation 11 | cocrystal of Production Example 1 | 100 | 1.3 (0.7) | 229.0 (106.5) | 585.5 (231.6) |

*[1] dose as compound (A)

INDUSTRIAL APPLICABILITY

The cocrystal of the present invention is superior in the dissolution property and oral absorbability, and is useful as a material of a medicament (pharmaceutical composition or formulation).

This application is based on a patent application No. 2015-252658 filed in Japan, the contents of which are incorporated in full herein.

The invention claimed is:

1. A cocrystal of (S)-3-(1-((1-acryloylpyrrolidin-3-yl)oxy)isoquinolin-3-yl)-1H-1,2,4-triazol-5(4H)-one and gentisic acid, wherein the cocrystal shows a powder X-ray diffraction pattern having characteristic peaks at lattice spacings (d) of 13.04±0.2, 5.96±0.2, 4.67±0.2, 3.63±0.2 and 3.28±0.2 angstroms.

2. The cocrystal according to claim 1, wherein a molar ratio of (S)-3-(1-((1-acryloylpyrrolidin-3-yl)oxy)isoquinolin-3-yl)-1H-1,2,4-triazol-5(4H)-one and gentisic acid ((S)-3-(1-((1-acryloylpyrrolidin-3-yl)oxy)isoquinolin-3-yl)-1H-1,2,4-triazol-5(4H)-one:gentisic acid) is 1:1.

3. A method of producing the cocrystal according to claim 1, comprising mixing and stirring a strongly basic aqueous solution of (S)-3-(1-((1-acryloylpyrrolidin-3-yl)oxy)isoquinolin-3-yl)-1H-1,2,4-triazol-5(4H)-one, and a solution of gentisic acid.

4. The production method according to claim 3, wherein the gentisic acid in the mixed solution of the strongly basic aqueous solution of (S)-3-(1-((1-acryloylpyrrolidin-3-yl)oxy)isoquinolin-3-yl)-1H-1,2,4-triazol-5(4H)-one and the solution of the gentisic acid has a concentration of 0.298-0.592 mol/L.

5. The production method according to claim 3, wherein the gentisic acid in the mixed solution of the strongly basic aqueous solution of (S)-3-(1-((1-acryloylpyrrolidin-3-yl)oxy)isoquinolin-3-yl)-1H-1,2,4-triazol-5(4H)-one and the solution of the gentisic acid has a concentration of 0.388-0.592 mol/L.

6. The production method according to claim 3, wherein a solvent of the solution of the gentisic acid is
   (i) water,
   (ii) at least one organic solvent selected from the group consisting of isopropyl alcohol, dimethyl sulfoxide, N,N-dimethylformamide, N,N-dimethylacetamide, methanol, ethanol, 1-propanol, tetrahydrofuran, acetone, 2,2,2-trifluoroethanol, acetonitrile, 1-methyl-2-pyrrolidone, and acetic acid, or
   (iii) a mixed solvent of at least one organic solvent selected from the group described in (ii) and water.

7. The production method according to claim 3, comprising adding, as a seed crystal, a cocrystal of (S)-3-(1-((1-acryloylpyrrolidin-3-yl)oxy)isoquinolin-3-yl)-1H-1,2,4-triazol-5(4H)-one and gentisic acid to the mixture of the strongly basic aqueous solution of (S)-3-(1-((1-acryloylpyrrolidin-3-yl)oxy)isoquinolin-3-yl)-1H-1,2,4-triazol-5 (4H)-one and the solution of the gentisic acid.

8. The cocrystal according to claim 1, wherein the cocrystal shows a powder X-ray diffraction pattern having characteristic peaks at lattice spacings (d) of 13.04±0.2, 10.92±0.2, 9.97±0.2, 5.96±0.2, 4.67±0.2, 3.63±0.2 and 3.28±0.2 angstroms.

9. The cocrystal according to claim 1, wherein the cocrystal shows a powder X-ray diffraction pattern having characteristic peaks at lattice spacings (d) of 13.04±0.2, 10.92±0.2, 9.97±0.2, 6.14±0.2, 5.96±0.2, 5.28±0.2, 4.67±0.2, 3.63±0.2 and 3.28±0.2 angstroms.

10. The cocrystal according to claim 1, wherein the cocrystal is a nonhydrate.

* * * * *

UNITED STATES PATENT AND TRADEMARK OFFICE
CERTIFICATE OF CORRECTION

| | | |
|---|---|---|
| PATENT NO. | : 10,836,745 B2 | Page 1 of 1 |
| APPLICATION NO. | : 15/388063 | |
| DATED | : November 17, 2020 | |
| INVENTOR(S) | : Kimoto et al. | |

It is certified that error appears in the above-identified patent and that said Letters Patent is hereby corrected as shown below:

On the Title Page:

The first or sole Notice should read --

Subject to any disclaimer, the term of this patent is extended or adjusted under 35 U.S.C. 154(b) by 43 days.

Signed and Sealed this
Twenty-third Day of November, 2021

Drew Hirshfeld
*Performing the Functions and Duties of the*
*Under Secretary of Commerce for Intellectual Property and*
*Director of the United States Patent and Trademark Office*